US012760031B2

(12) United States Patent
Krautwald et al.

(10) Patent No.: US 12,760,031 B2
(45) Date of Patent: Oct. 13, 2026

(54) PYRIDINE-3-CARBOXYLATE COMPOUNDS AS $CA_V$1.2 ACTIVATORS

(71) Applicant: Novartis AG, Basel (CH)

(72) Inventors: Simon Krautwald, Cambridge, MA (US); Jianliang Lu, Cambridge, MA (US); James Anthony Neef, Stow, MA (US); Tejaskumar Pankajbhai Pathak, Belmont, MA (US); Amir Masoud Sadaghiani, Dover, MA (US); Xilin Zhou, Arlington, MA (US)

(73) Assignee: Novartis AG, Basel (CH)

(*) Notice: Subject to any disclaimer, the term of this patent is extended or adjusted under 35 U.S.C. 154(b) by 198 days.

(21) Appl. No.: 18/718,953

(22) PCT Filed: Dec. 12, 2022

(86) PCT No.: PCT/IB2022/062037
§ 371 (c)(1),
(2) Date: Jun. 12, 2024

(87) PCT Pub. No.: WO2023/111799
PCT Pub. Date: Jun. 22, 2023

(65) Prior Publication Data

US 2025/0051345 A1 Feb. 13, 2025

Related U.S. Application Data

(60) Provisional application No. 63/265,302, filed on Dec. 13, 2021.

(51) Int. Cl.
*C07D 491/048* (2006.01)
*A61K 31/444* (2006.01)

(52) U.S. Cl.
CPC ........ *C07D 491/048* (2013.01); *A61K 31/444* (2013.01)

(58) Field of Classification Search
CPC ............................ C07D 491/48; A61K 31/444
USPC ......................................................... 514/302
See application file for complete search history.

(56) References Cited

FOREIGN PATENT DOCUMENTS

| | | | |
|---|---|---|---|
| GB | 2105989 | A | 4/1983 |
| WO | 2021/253180 | A1 | 12/2021 |

OTHER PUBLICATIONS

Skrastin'Sh et al., Synthesis and pharmacological activity of furo-1,4-dihydropyridines. Pharmaceutical Chemistry Journal. 1989;23:893-896.

International Search Report and Written Opinion for Application No. PCT/IB2022/062037, dated Feb. 13, 2023, 10 pages.

*Primary Examiner* — Kahsay Habte

(74) *Attorney, Agent, or Firm* — McCarter & English, LLP; Michael J. DeGrazia

(57) ABSTRACT

The present disclosure provides for a compound according to formula (I) or a pharmaceutically acceptable salt thereof as $Ca_v$1.2 activators for the treatment of schizophrenia, bipolar disorder, major depressive disorder, substance use disorder. ADHD, Phelan-Mc-Dermid Syndrome, autism spectrum disorder, multiple sclerosis, frontotemporal dementia, Alzheimer's disease. Brugada Syndrome. Short QT syndrome, or early repolarization syndrome.

(I)

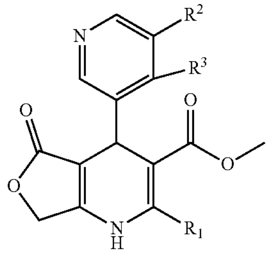

17 Claims, 2 Drawing Sheets

PYRIDINE-3-CARBOXYLATE COMPOUNDS AS $CA_V1.2$ ACTIVATORS

CROSS REFERENCE TO RELATED APPLICATIONS

This application is a U.S. National Stage Application filed under 35 U.S.C. § 371, based on International Patent Application No. PCT/IB2022/062037, filed on Dec. 12, 2022, which claims priority to U.S. Provisional Application No. 63/265,302, filed on Dec. 13, 2021. The entire contents of each of the above applications are incorporated herein by reference.

1. FIELD OF THE INVENTION

The present disclosure relates to pyridine-3-carboxylate compounds, pharmaceutical compositions containing them, and the use of such compounds as $Ca_v1.2$ activators for the treatment of calcium signaling deficit and/or synaptic dysfunction in psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome.

2. BACKGROUND OF THE INVENTION

Advancements in human genomics have shed light on the genetic basis of psychiatric disorders. Genome wide association studies (GWAS) in schizophrenia have identified over one hundred disease-associated loci, including $Ca_v1.2$ and other genes involved in neuronal calcium signaling. A cross-disorder GWAS analysis has identified $Ca_v1.2$ and its channel-forming beta subunit (CACNB2) as strongly associated with schizophrenia, bipolar disorder, major depressive disorder, ADHD, and autism spectrum disorders. In addition to evidence from GWAS, exome sequencing in patients with schizophrenia showed enrichment of disruptive mutations in $Ca_v1.2$ and other gene members of the neuronal calcium-signaling pathway including the CACNA2D, CACNB, CAMK2 genes. $Ca_v1.2$ has been shown to be important for neuronal differentiation and migration, neurite outgrowth, synaptic signaling, gene expression and brain plasticity. It has been shown to play a role in emotion, learning and memory, executive function, and reward responses of the brain.

$Ca_v1.2$ is broadly expressed throughout the body and plays a major role in multiple organ systems including the cardiovascular system; however, the physiological function of $Ca_v1.2$ in the cardiovascular system is distinct from its function in the brain. Studies have shown that $Ca_v1.2$ is a key contributor to action potential generation in the heart while it is a key driver of intracellular signaling and gene expression in neurons with minimal role in action potential generation. In Timothy Syndrome, $Ca_v1.2$ mutation p.G406R leads to distinct cellular phenotypes between cardiomyocytes and neurons. $Ca_v1.2$ mutations that cause cardiovascular specific disorders (Brugada Syndrome and Long QT syndrome type 8) are further evidence for the divergent functions of $Ca_v1.2$ in heart and brain.

Calcium channel activators have been previously reported, but further investigation into their use for neuropsychiatric disorders has been limited due to their effects on the cardiovascular system. In fact, many of these molecules were initially investigated and developed for their potential therapeutic use in heart failure. Most of the $Ca_v1.2$ SNPs associated from psychiatric GWAS studies reside in introns of the gene, and these risk SNPs have been shown to be associated with reduction of mRNA expression that in many cases results in overall reduction of calcium current amplitude. Therefore, small molecules that can increase the overall current amplitude could be the most beneficial to patients.

3. SUMMARY OF THE INVENTION

The present disclosure provides for a compound according to formula (I) or a pharmaceutically acceptable salt thereof

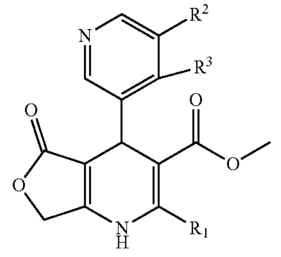

(I)

wherein:

$R^1$ is selected from $C_{1-6}$ alkyl and $C_{1-6}$ haloalkyl, e.g., $C_{1-6}$ fluoroalkyl;

$R^2$ is selected from H and halo, e.g., F; and $R^3$ is selected from $C_{1-6}$ alkyl, e.g., $C_{1-4}$ alkyl, and $C_{3-8}$ cycloalkyl, each of which is optionally substituted with one to three halo, e.g., F.

In a second aspect, the disclosure provides a pharmaceutical composition comprising a compound of formula (I) or a pharmaceutically acceptable salt thereof.

In a third aspect, the disclosure provides for a compound of formula (I), or a pharmaceutically acceptable salt thereof, for use in therapy, in particular in the treatment of psychiatric disorders including schizophrenia, bipolar disorder, major depressive disorder, or substance use disorders; neurodevelopmental disorders, such as attention deficit hyperactivity disorder, Phelan-McDermid Syndrome, or other autism spectrum disorders; neurodegenerative disorders, such as multiple sclerosis, frontotemporal dementia or Alzheimer's disease; and cardiac conditions such as Brugada Syndrome, Short QT syndrome, or early repolarization syndrome.

In a fourth aspect, the disclosure provides a method of treating psychiatric disorders, such as schizophrenia, bipolar disorder, major depressive disorder, or substance use disorder; neurodevelopmental disorders, such as ADHD, Phelan McDermid Syndrome, or autism spectrum disorder; neurodegenerative disorders, such as multiple sclerosis, frontotemporal dementia, or Alzheimer's disease; or cardiac conditions such as Brugada Syndrome, Short QT syndrome, or early repolarization syndrome in a subject in need thereof, the method comprising administering a therapeutically effective amount of a compound of the present disclosure, or a pharmaceutically acceptable salt thereof.

In a fifth aspect, the disclosure provides a method of treating psychiatric disorders, such as schizophrenia, bipolar disorder, major depressive disorder, or substance use disorder; neurodevelopmental disorders, such as ADHD, Phelan McDermid Syndrome, or autism spectrum disorder; neurodegenerative disorders, such as multiple sclerosis, frontotemporal dementia, or Alzheimer's disease; or cardiac conditions such as Brugada Syndrome, Short QT syndrome, or early repolarization syndrome in a subject in need thereof, the method comprising administering a compound of the present disclosure, or a pharmaceutically acceptable salt thereof.

In a sixth aspect, the disclosure provides a use of a compound of the present disclosure, or a pharmaceutically acceptable salt thereof, in the manufacture of a medicament for the treatment of psychiatric disorders, such as schizophrenia, bipolar disorder, major depressive disorder, or substance use disorder; neurodevelopmental disorders, such as ADHD, Phelan McDermid Syndrome, or autism spectrum disorder; neurodegenerative disorders, such as multiple sclerosis, frontotemporal dementia, or Alzheimer's disease; or cardiac conditions such as Brugada Syndrome, Short QT syndrome, or early repolarization syndrome.

4. BRIEF DESCRIPTION OF THE DRAWINGS

5. DETAILED DESCRIPTION OF THE INVENTION

5.1. Definitions

Figure 1:
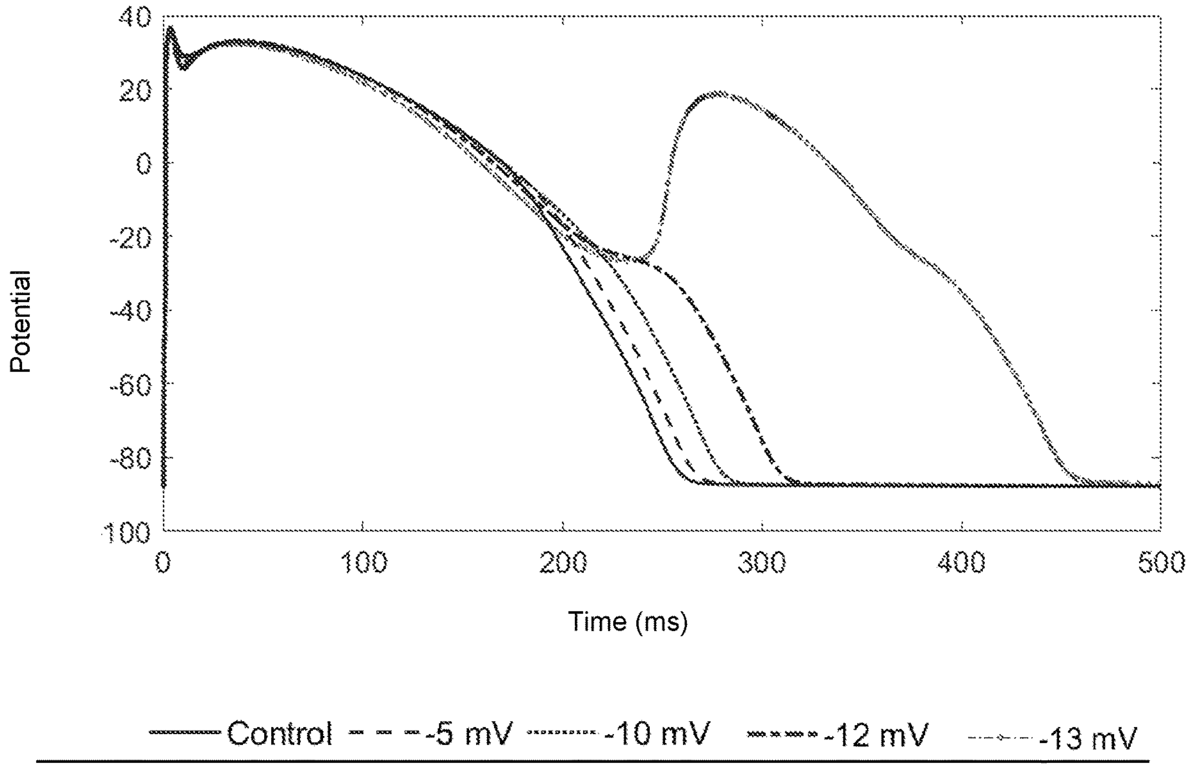
FIG. 1 is a graph illustrating a simulated cardiac action potentials from an epicardial environment showing the impact of shifting the voltage of $Ca_v1.2$ activation to more negative membrane potentials at a Potential (mV) versus Time (ms).

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

Unless specified otherwise, the terms "compounds of the present disclosure", "compounds of the disclosure", or "compound of the disclosure" refer to compounds of formula (I), (II), (Ia), or (Ib), exemplified compounds, salts thereof, particularly pharmaceutically acceptable salts thereof, hydrates, solvates, as well as all stereoisomers (including diastereoisomers and enantiomers), rotamers, tautomers, and isotopically labeled compounds (including deuterium substitutions), as well as inherently formed moieties.

The term "and/or" means either "and" or "or" unless indicated otherwise.

The term "substituted" means that the specified group or moiety bears one or more suitable substituents wherein the substituents may connect to the specified group or moiety at one or more positions. For example, a cyclopropyl substituted with a fluoro group (F) indicates that the fluoro connects to one atom of the cyclopropyl with a bond.

As used herein the term "$C_{1-6}$ alkyl" refers to a straight or branched hydrocarbon chain radical consisting solely of carbon and hydrogen atoms, containing no unsaturation, having from one to six carbon atoms, and which is attached to the rest of the molecule by a single bond. Examples of $C_{1-6}$ alkyl include, without limitations, methyl, ethyl, n-propyl, 1-methylethyl (iso-propyl), n-butyl, 1-methylpropyl (sec-butyl), 2-methylpropyl (iso-butyl), 1,1-dimethylethyl (t-butyl), n-pentyl, and n-hexyl. The term $C_{1-4}$ alkyl is to be construed accordingly.

As used herein, the term "$C_{1-6}$ haloalkyl" refers to a $C_{1-6}$ alkyl radical, as defined above, substituted by one or more halo radicals, as defined herein. Examples of $C_{1-6}$ haloalkyl include, without limitations, trifluoromethyl, difluoromethyl, fluoromethyl, trichloromethyl, 1,1-difluoroethyl, 2,2-difluoroethyl, 2,2,2-trifluoroethyl, 2-fluoropropyl, 3,3-difluoropropyl and 1-fluoromethyl-2-fluoroethyl, 1,3-dibromopropan-2-yl, 3-bromo-2-fluoropropyl, and 1,4,4-trifluorobutan-2-yl.

As used herein, the term "halo" means fluorine, chlorine, bromine or iodine.

As used herein, the term "cycloalkyl" means a monocyclic or polycyclic saturated or partially unsaturated carbon ring containing 3-18 carbon atoms wherein there are no delocalized pi electrons (aromaticity) shared among the ring carbons. The term "$C_{3-8}$ cycloalkyl" is to be construed accordingly. The term polycyclic encompasses bridged (e.g., norbornane), fused (e.g., decalin) and spirocyclic cycloalkyl. Preferably, cycloalkyl, e.g., "$C_{3-8}$ cycloalkyl", is a monocyclic hydrocarbon group of 3 to 8 carbon atoms.

Examples of $C_{3-8}$ cycloalkyl include, without limitations, cyclopropyl, cyclobutyl, cyclopentyl, cyclohexyl, cycloheptyl, spiro[3.3]heptanyl, and cyclooctyl.

As used herein, "administer" refers to the manner in which a compound described herein is presented to a subject.

As used herein, "optionally substituted" means the group referred to can be substituted at one or more positions by any one or any combination of the radicals listed thereafter.

As used herein, "subject" or "patient" refers to a living organism suffering from one or more of the diseases or disorders described here (e.g., psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome) that can be treated by administration of a pharmaceutical composition described herein. Examples of subjects include mammals (e.g., humans and animals such as dogs, cows, horses, monkeys, pigs, sheep, goats, cats, mice, rabbits, rats, and transgenic non-human animals). In certain embodiments, the subject is a human, e.g., a human suffering from, at risk of suffering from, or potentially capable of suffering from a disease described herein (e.g., psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

If there is a discrepancy between a depicted structure and a chemical name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure of portion of the structure.

5.2. Compounds

A compound according to formula (I) or a pharmaceutically acceptable salt thereof (I)

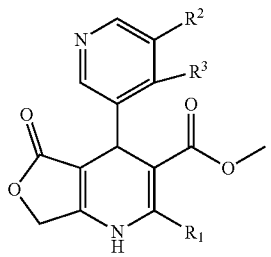

wherein:

$R^1$ is selected from $C_{1-6}$ alkyl and $C_{1-6}$ haloalkyl, e.g., $C_{1-6}$ fluoroalkyl;

$R^2$ is selected from H and halo, e.g., F; and $R^3$ is selected from $C_{1-6}$ alkyl, e.g., $C_{1-4}$ alkyl, and $C_{3-8}$ cycloalkyl, each of which is optionally substituted with one to three halo, e.g., F.

One embodiment is a compound according to formula (I) or a pharmaceutically acceptable salt thereof (I)

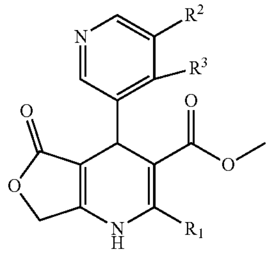

wherein:

$R^1$ is selected from $CH_3$, $CF_3$, $CHF_2$, and $CH_2F$;

$R^2$ is selected from H and F; and $R^3$ is selected from $C_{1-4}$ alkyl, cyclopropyl, and cyclobutyl each of which is optionally substituted with one to three F.

One embodiment is a compound of formula (Ia)

(Ia)

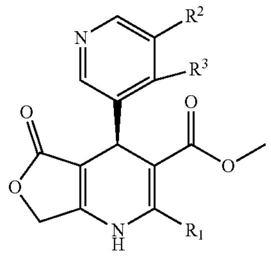

or a pharmaceutically acceptable salt thereof.

Another embodiment is a compound of formula (Ib)

(Ib)

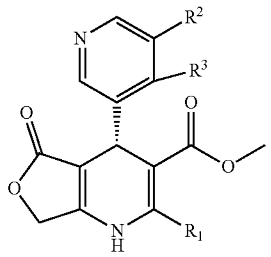

or a pharmaceutically acceptable salt thereof.

The following embodiments are in relation to a compound of formula (I), including formula (Ia) and (Ib):

In one embodiment, $R^1$ is $CH_3$.

In another embodiment, $R^1$ is $CF_3$.

In another embodiment, $R^1$ is $CHF_2$.

In another embodiment, $R^1$ is $CH_2F$.

In another embodiment, $R^2$ is H.

In another embodiment, $R^2$ is F.

In another embodiment, $R^3$ is $C_{1-4}$ alkyl which is optionally substituted with one to three F.

In another embodiment, $R^3$ is cyclopropyl which is optionally substituted with one to three F.

In another embodiment, $R^3$ is cyclobutyl which is optionally substituted with one to three F.

Specific compounds of formula (I) include:

methyl 4-(5-fluoro-4-(1-fluoroethyl) pyridin-3-yl)-2-methyl-5-oxo-1,4,5,7-tetrahydrofuro [3,4-b]pyridine-3-carboxylate;

methyl(S)-4-(5-fluoro-4-((R)-1-fluoroethyl) pyridin-3-yl)-2-methyl-5-oxo-1,4,5,7-tetrahydrofuro [3,4-b]pyridine-3-carboxylate;

methyl(S)-4-(5-fluoro-4-((S)-1-fluoroethyl) pyridin-3-yl)-2-methyl-5-oxo-1,4,5,7-tetrahydrofuro [3,4-b]pyridine-3-carboxylate;

methyl (R)-4-(5-fluoro-4-((R)-1-fluoroethyl) pyridin-3-yl)-2-methyl-5-oxo-1,4,5,7-tetrahydrofuro [3,4-b]pyridine-3-carboxylate;

methyl (R)-4-(5-fluoro-4-((S)-1-fluoroethyl) pyridin-3-yl)-2-methyl-5-oxo-1,4,5,7-tetrahydrofuro [3,4-b]pyridine-3-carboxylate;

methyl 4-(5-fluoro-4-(1-fluoroethyl) pyridin-3-yl)-2-(fluoromethyl)-5-oxo-1,4,5,7-tetrahydrofuro [3,4-b] pyridine-3-carboxylate;

methyl (R)-4-(5-fluoro-4-((R)-1-fluoroethyl) pyridin-3-yl)-2-(fluoromethyl)-5-oxo-1,4,5,7-tetrahydrofuro [3,4-b]pyridine-3-carboxylate;

methyl (R)-4-(5-fluoro-4-((S)-1-fluoroethyl) pyridin-3-yl)-2-(fluoromethyl)-5-oxo-1,4,5,7-tetrahydrofuro [3,4-b]pyridine-3-carboxylate;

methyl(S)-4-(5-fluoro-4-((R)-1-fluoroethyl) pyridin-3-yl)-2-(fluoromethyl)-5-oxo-1,4,5,7-tetrahydrofuro [3,4-b]pyridine-3-carboxylate;

methyl(S)-4-(5-fluoro-4-((S)-1-fluoroethyl) pyridin-3-yl)-2-(fluoromethyl)-5-oxo-1,4,5,7-tetrahydrofuro [3,4-b]pyridine-3-carboxylate;

methyl 4-(4-ethyl-5-fluoropyridin-3-yl)-2-(fluoromethyl)-5-oxo-1,4,5,7-tetrahydrofuro [3,4-b]pyridine-3-carboxylate;

methyl (R)-4-(4-ethyl-5-fluoropyridin-3-yl)-2-(fluoromethyl)-5-oxo-1,4,5,7-tetrahydrofuro [3,4-b]pyridine-3-carboxylate;

methyl(S)-4-(4-ethyl-5-fluoropyridin-3-yl)-2-(fluoromethyl)-5-oxo-1,4,5,7-tetrahydrofuro [3,4-b]pyridine-3-carboxylate;

methyl 4-(4-ethyl-5-fluoropyridin-3-yl)-2-methyl-5-oxo-1,4,5,7-tetrahydrofuro [3,4-b]pyridine-3-carboxylate;

methyl(S)-4-(4-ethyl-5-fluoropyridin-3-yl)-2-methyl-5-oxo-1,4,5,7-tetrahydrofuro [3,4-b]pyridine-3-carboxylate;

methyl (R)-4-(4-ethyl-5-fluoropyridin-3-yl)-2-methyl-5-oxo-1,4,5,7-tetrahydrofuro [3,4-b]pyridine-3-carboxylate;

methyl 4-(4-ethylpyridin-3-yl)-2-(fluoromethyl)-5-oxo-1,4,5,7-tetrahydrofuro [3,4-b]pyridine-3-carboxylate;

methyl (R)-4-(4-ethylpyridin-3-yl)-2-(fluoromethyl)-5-oxo-1,4,5,7-tetrahydrofuro [3,4-b]pyridine-3-carboxylate;

methyl(S)-4-(4-ethylpyridin-3-yl)-2-(fluoromethyl)-5-oxo-1,4,5,7-tetrahydrofuro [3,4-b]pyridine-3-carboxylate;

methyl 2-(difluoromethyl)-4-(5-fluoro-4-(1-fluoroethyl) pyridin-3-yl)-5-oxo-1,4,5,7-tetrahydrofuro [3,4-b]pyridine-3-carboxylate;

methyl (R)-2-(difluoromethyl)-4-(5-fluoro-4-((R)-1-fluoroethyl) pyridin-3-yl)-5-oxo-1,4,5,7-tetrahydrofuro [3,4-b]pyridine-3-carboxylate;

methyl (R)-2-(difluoromethyl)-4-(5-fluoro-4-((S)-1-fluoroethyl) pyridin-3-yl)-5-oxo-1,4,5,7-tetrahydrofuro [3,4-b]pyridine-3-carboxylate;

methyl(S)-2-(difluoromethyl)-4-(5-fluoro-4-((R)-1-fluoroethyl) pyridin-3-yl)-5-oxo-1,4,5,7-tetrahydrofuro [3,4-b]pyridine-3-carboxylate;

methyl(S)-2-(difluoromethyl)-4-(5-fluoro-4-((S)-1-fluoroethyl) pyridin-3-yl)-5-oxo-1,4,5,7-tetrahydrofuro [3,4-b]pyridine-3-carboxylate;

methyl 4-(5,6-difluoro-4-(1-fluoroethyl) pyridin-3-yl)-2-methyl-5-oxo-1,4,5,7-tetrahydrofuro [3,4-b]pyridine-3-carboxylate;

methyl(S)-4-(5,6-difluoro-4-((R)-1-fluoroethyl) pyridin-3-yl)-2-methyl-5-oxo-1,4,5,7-tetrahydrofuro [3,4-b] pyridine-3-carboxylate;

methyl(S)-4-(5,6-difluoro-4-((S)-1-fluoroethyl) pyridin-3-yl)-2-methyl-5-oxo-1,4,5,7-tetrahydrofuro [3,4-b] pyridine-3-carboxylate;

methyl (R)-4-(5,6-difluoro-4-((R)-1-fluoroethyl) pyridin-3-yl)-2-methyl-5-oxo-1,4,5,7-tetrahydrofuro [3,4-b] pyridine-3-carboxylate; and methyl (R)-4-(5,6-difluoro-4-((S)-1-fluoroethyl) pyridin-3-yl)-2-methyl-5-oxo-1,4,5,7-tetrahydrofuro [3,4-b] pyridine-3-carboxylate.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present disclosure is meant to include all such possible stereoisomers, including racemic mixtures, diasteriomeric mixtures and optically pure forms. Optically active (R)- and(S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the present disclosure. "Salts" include in particular "pharmaceutically acceptable salts". The term "pharmaceutically acceptable salts" refers to salts that retain the biological effectiveness and properties of the compounds of this disclosure and, which typically are not biologically or otherwise undesirable. In many cases, the compounds of the present disclosure are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present disclosure provides compounds of the present disclosure in acetate, ascorbate, adipate, benzoate, aspartate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Compounds of the disclosure, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the disclosure further provides co-crystals comprising a compound of formula (I).

Furthermore, the compounds of the present disclosure, including their salts, can also be obtained in the form of their hydrates, or include other solvents used for their crystallization. The compounds of the present disclosure may inherently or by design form solvates with pharmaceutically acceptable solvents (including water); therefore, it is intended that the disclosure embrace both solvated and unsolvated forms. The term "solvate" refers to a molecular complex of a compound of the present disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The disclosure includes unlabeled forms as well as isotopically labeled forms of compounds of formula (I). Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen.

Further, incorporation of certain isotopes, particularly deuterium (i.e., 2H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present disclosure. The concentration of deuterium, may be defined by the isotopic enrichment factor. The term "isotopic enrichment factor" as used herein means the ratio between the isotopic abundance and the natural abundance of a specified isotope. If a substituent in a compound of this disclosure is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

In one embodiment of any aspect of the present disclosure, the hydrogens in the compound of Formula (I) are present in their normal isotopic abundances. In another embodiment, the hydrogens are isotopically enriched in deuterium (D), and in a particular embodiment of the disclosure, formula (I) is deuterated as shown in formula (II):

(II)

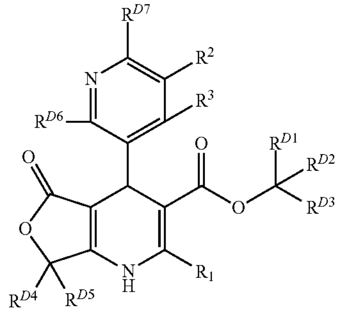

or a pharmaceutically acceptable salt thereof, wherein $R^1$, $R^2$ and $R^3$ are as defined in formula (I) according to any aspect or embodiment of the present disclosure; $R^{D1}$ through $R^{D7}$ are each independently H or D. Compound of formula (II) can be synthesized according to any one of General Schemes 1 to 2 by employing the appropriate deuterated substrate in place of the non-deuterated version.

Other examples of isotopes that can be incorporated into compounds of the disclosure include isotopes of hydrogen, carbon, nitrogen, oxygen, and fluorine, such as $^3H$, $^{11}C$, $^{13}C$, $^{14}C$, $^{15}N$, $^{18}F$, and $^{18}O$, respectively. Accordingly it should be understood that the disclosure includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of the present disclosure can generally be prepared by conventional techniques known to those skilled in the art or by processes analogous to those described in the accompanying Examples and Preparations using an appropriate isotopically-labeled reagents in place of the non-labeled reagent previously employed.

Any asymmetric atom (e.g., carbon or the like) of the compound(s) of the present disclosure can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or(S)-configuration.

Accordingly, as used herein a compound of the present disclosure can be in the form of one of the possible stereoisomers, rotamers, atropisomers, tautomers or mixtures thereof, for example, as substantially pure diastereomers, optical isomers (antipodes), racemates or mixtures thereof.

Thus, compounds of the disclosure can be present in a racemic mixture or in enantiomerically enriched form or in an enantiopure form or as a mixture of diastereoisomers.

In the compound formulae in any one of the aspects, embodiments or claims of the present application the term "" on a C-$sp^3$ indicates the absolute stereochemistry, either (R) or(S). In the compound formulae in any one of the aspects, embodiments or claims of the present application the term “ ” on a C-$sp^3$ indicates the absolute stereochemistry, either (R) or(S). In the compound formulae in any one of the aspects, embodiments or claims of the present application the term “ ” on a C-$sp^3$ represents a covalent bond wherein the absolute stereochemistry of the bond is not defined. This means that the term “ ” on a C-$sp^3$ comprises an(S) configuration or an (R) configuration of the respective chiral centre or a mixture thereof. Therefore, mixtures of stereoisomers, e.g., mixtures of enantiomers, such as racemates, and/or mixtures of diastereoisomers are encompassed by the present disclosure.

Any resulting mixtures of stereoisomers can be separated on the basis of the physicochemical differences of the constituents, into the pure or substantially pure optical isomers, diastereomers, racemates, for example, by chromatography and/or fractional crystallization.

Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical isomers, e.g., by fractional crystallization of a salt formed with an optically active acid, e.g., tartaric acid, dibenzoyl tartaric acid, diacetyl tartaric acid, di-O, O'-p-toluoyl tartaric acid, mandelic acid, malic acid or camphor-10-sulfonic acid. Racemic compounds of the present disclosure or racemic intermediates can also be resolved by chiral chromatography, e.g., high pressure liquid chromatography (HPLC) using a chiral adsorbent.

5.3. Methods of Making

The compounds of the disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Generally, the compounds of formula (I) can be prepared according to the Schemes provided infra.

-continued

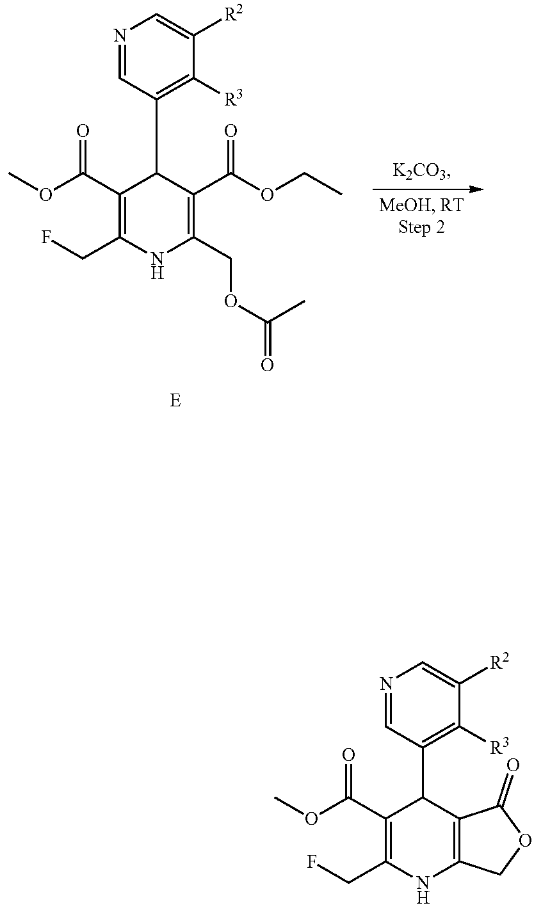

The starting materials for the above reaction scheme are commercially available or can be prepared according to methods known to one skilled in the art or by methods disclosed herein. In general, the compounds of the disclosure are prepared in the above General Scheme 1 as follows:

Compound (Y) is reacted with Intermediates A and B under condensation reaction conditions to afford compound E. Intramolecular lactonization with potassium carbonate and methanol affords a compound of Formula (I) ($R^1$=$CH_2F$). For General Scheme 1, $R^2$ and $R^3$ are as defined herein.

General Scheme 1

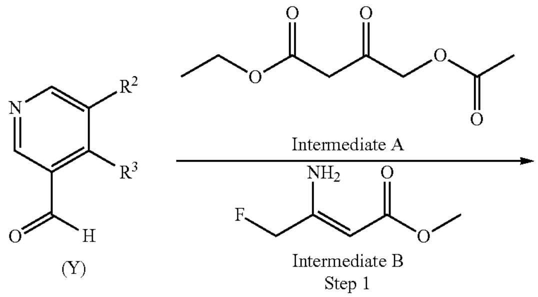

General Scheme 2

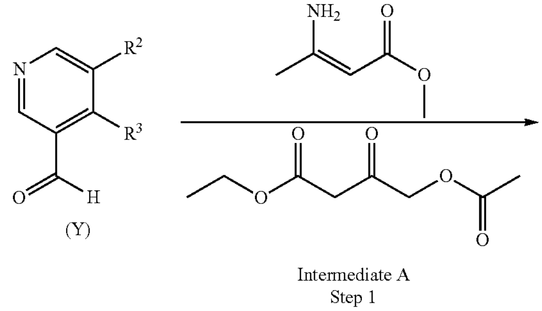

-continued

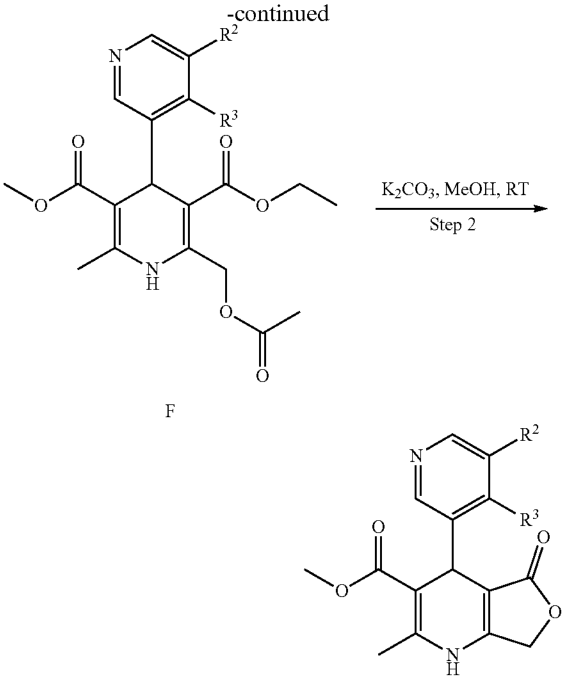

F (I)

Compound (Y) is reacted with intermediate A and methyl (Z)-3-aminobut-2-enoate under condensation reaction conditions to afford compound F. Intramolecular lactonization with potassium carbonate and methanol affords a compound of Formula (I) ($R^1$=$CH_3$). For General Scheme 2, $R^2$ and $R^3$ are as defined herein.

In an embodiment, there is provided a compound of formula (X) or a salt thereof, wherein:

(X)

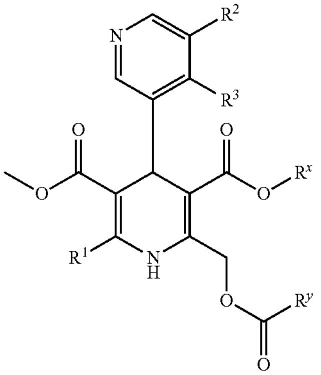

$R^1$ is selected from $CH_3$, $CF_3$, $CHF_2$ and $CH_2F$;

$R^2$ is selected from H and F;

$R^3$ is selected from $C_{1-4}$ alkyl, cyclopropyl and cyclobutyl each of which is optionally substituted with one to three F; and $R^x$ and $R^y$ are each independently $C_{1-6}$alkyl, e.g., $R^x$ is ethyl and $R^y$ is methyl.

In an embodiment, there is provided the use of a compound of formula (X) in the preparation of a compound of formula (I).

In a further embodiment, there is provided a compound of formula (Y) or a salt thereof, wherein:

(Y)

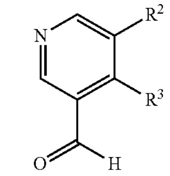

$R^2$ is selected from H and F; and $R^3$ is selected from $C_{1-4}$ alkyl, cyclopropyl and cyclobutyl each of which is optionally substituted with one to three F.

In an embodiment, there is provided the use of a compound of formula (Y) in the preparation of a compound of formula (I).

In a further aspect, the disclosure provides a process for the preparation of a compound of formula (I), in free form or in pharmaceutically acceptable salt form, comprising the step of:

1) Reacting a compound of formula (Y) as defined herein with

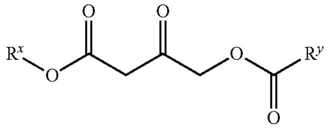

and

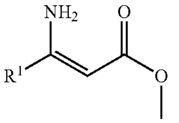

under condensation reaction conditions, e.g., heat, wherein $R^1$ is selected from $CH_3$, $CF_3$, $CHF_2$ and $CH_2F$; and $R^x$ and $R^y$ are each independently $C_{1-6}$ alkyl, e.g., $R^x$ is ethyl and $R^y$ is methyl, to produce a compound of formula (X) as defined herein.

In a further embodiment of the process for the preparation of a compound of formula (I), the process comprises the step of:

2) Reacting a compound of formula (X) as defined herein, e.g., prepared according to step 1, under lactonization conditions, e.g., base and solvent, e.g., $K_2CO_3$ and methanol, to produce a compound of formula (I) as defined herein.

In a further embodiment the process of step 2 additionally comprises the optional steps of 3) purifying the compound of formula (I) as defined herein; and (optionally)

4) separating the resultant stereoisomers, e.g., by chromatography, e.g., by chiral chromatography.

Condensation reaction conditions for any of the aforementioned process steps or hereinafter involve the use of a solvent, e.g., a protic solvent such as an alcohol, e.g., methanol, ethanol, and heating the substrate mixture. Certain reactions may require the addition of a base, e.g., NaOH, amine (Knoevenagel condensation). The reaction mixture can be heated to the appropriate temperature required for the reaction to proceed, e.g., rt to 100° C., e.g., 70 to 80° C.

In a further embodiment there is provided a process for the preparation of a compound of formula (I), in free form or in pharmaceutically acceptable salt form according to any one of General Schemes 1 to 2.

Lactonization reaction conditions for any of the aforementioned process steps or hereinafter involve the use of an appropriate reagent to produce a lactone group. For example, the lactonization conditions may involve the use of a base, e.g., $K_2CO_3$, and a solvent such as a protic solvent, e.g., methanol, ethanol. The reaction may be performed at room temperature or by heating, e.g., rt to 80° C.

Compounds of formulae (X) and (Y) as defined herein are useful in the preparation of compounds of the disclosure, e.g., compounds of (I). Thus, in an aspect, the disclosure relates to a compound of formula (X) or (Y), or salts thereof. In another aspect, the disclosure relates to the use of a compound of formula (X) or (Y), or salts thereof in the manufacture of a compound of formula (I). The disclosure further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

5.4. Methods of Use

The compounds of the present disclosure in free form or in pharmaceutically acceptable salt form, exhibit valuable pharmacological properties, e.g., $Ca_v1.2$ activation properties, e.g., as indicated in vitro and in vivo tests as provided in the next sections, and are therefore indicated for therapy or for use as research chemicals, e.g., as tool compounds.

Compounds of the present disclosure, e.g., a compound of formula (I) (including (II), (Ia) and (Ib)) may be useful in the treatment of an indication selected from the following list:

- psychiatric disorders, such as schizophrenia, bipolar disorder, major depressive disorder, and substance use disorders;
- neurodevelopmental disorders, such as attention deficit hyperactivity disorder, Phelan-McDermid Syndrome and other autism spectrum disorders;
- neurodegeneration disorders, such as multiple sclerosis, frontotemporal dementia and Alzheimer's disease; and
- cardiac conditions, such as Brugada Syndrome, Short QT syndrome, and early repolarization syndrome. In one embodiment, the indication is a psychiatric disorder such as schizophrenia, bipolar disorder, major depressive disorder, or substance use disorders. In another embodiment, the indication is schizophrenia or bipolar disorder.

In another aspect, the disclosure provides a method of treating a disease or disorder which is treated by activation of $Ca_v1.2$ comprising administration of a therapeutically effective amount of a compound of the present disclosure or a pharmaceutically acceptable salt thereof. In a further embodiment, the disease is selected from the afore-mentioned list of indications.

In another aspect, the disclosure provides a method of treating a disease or disorder which is treated by activation of $Ca_v1.2$ comprising administration of a compound of the present disclosure or a pharmaceutically acceptable salt thereof. In a further embodiment, the disease is selected from the afore-mentioned list of indications.

In another aspect, the present disclosure provides a method of treating schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome in a subject in need thereof, the method comprising administering a therapeutically effective amount of a compound of the present disclosure, e.g., a compound of formula (I), or a pharmaceutically acceptable salt thereof.

In another aspect, the present disclosure provides a method of treating schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome in a subject in need thereof, the method comprising administering a compound of the present disclosure, e.g., a compound of formula (1), or a pharmaceutically acceptable salt thereof.

In a further aspect, the present disclosure provides a compound of the present disclosure, e.g., a compound of formula (I), or a pharmaceutically acceptable salt thereof, for use in therapy. In a further embodiment, the therapy is selected from a disease or disorder which may be treated by activation of $Ca_v1.2$. In another embodiment, the disease is selected from the afore-mentioned list of indications.

In a further aspect, the present disclosure provides a compound of the present disclosure, e.g., a compound of formula (I), or a pharmaceutically acceptable salt thereof, for use in treating schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

Thus, in a further aspect, the present disclosure provides the use of a compound of the present disclosure, e.g., a compound of formula (I), or a pharmaceutically acceptable salt thereof, in therapy. In a further embodiment, the therapy is selected from a disease which may be treated by activation of $Ca_v1.2$. In another embodiment, the disease is selected from the afore-mentioned list of indications.

In a further aspect, the present disclosure provides the use of a compound of the present disclosure, e.g., a compound of formula (I), or a pharmaceutically acceptable salt thereof, for the manufacture of a medicament. In a further embodiment, the medicament is for treatment of a disease which may be treated by activation of $Ca_v1.2$. In another embodiment, the disease is selected from the afore-mentioned list of indications.

In a further aspect, the present disclosure provides the use of a compound of the present disclosure, e.g., a compound of formula (I), or a pharmaceutically acceptable salt thereof, for the manufacture of a medicament for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

Thus, in a further aspect, the present disclosure provides the use of a compound of the present disclosure, e.g., a compound of formula (I), or a pharmaceutically acceptable salt thereof, for treating schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

All the aforementioned embodiments and embodiments hereinafter relating to the uses, methods of treatment and compounds for use are equally applicable to a pharmaceutical composition comprising a compound of the present disclosure, e.g., a compound of formula (I), or a pharmaceutically acceptable salt thereof.

5.5. Pharmaceutical Compositions

In another aspect, the present disclosure provides a pharmaceutical composition comprising a compound of the present disclosure, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g., by injection, infusion, transdermal or topical administration), and rectal administration. Topical administration may also pertain to inhalation or intranasal application. The pharmaceutical compositions of the present disclosure can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

The pharmaceutical composition of the present disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

6. Preparation of Compounds

The following examples are intended to illustrate the disclosure and are not to be construed as being limitations thereon.

Figure 2:
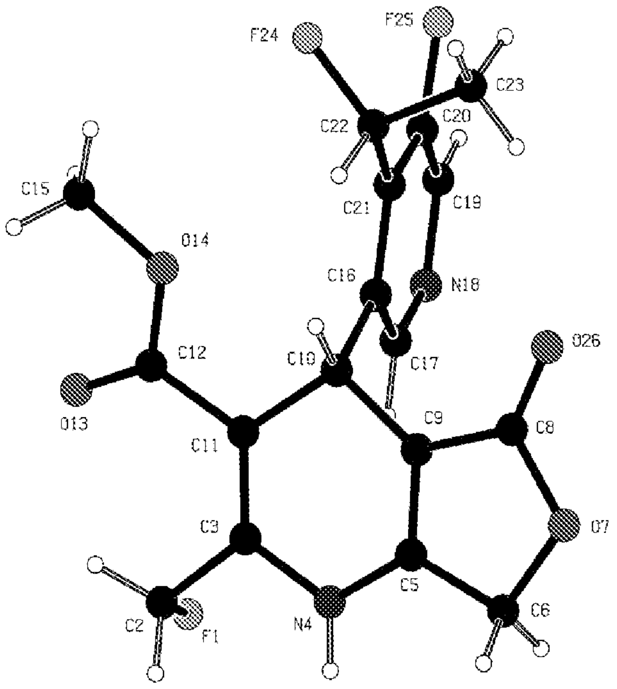
FIG. 2 is an image showing an X-ray crystal structure of Example 2.

The examples were all separated into their single enantiomers and were tested in the Sophion QPatch assay described in the Biological Data section below. The absolute stereochemistry of Example 2, methyl (R)-4-(5-fluoro-4-((R)-1-fluoroethyl) pyridin-3-yl)-2-(fluoromethyl)-5-oxo-1,4,5,7-tetrahydrofuro [3,4-b]pyridine-3-carboxylate was determined by single crystal x-ray crystallographic analysis (FIG. 2). The methyl (R)-4-(5-fluoro-4-((R)-1-fluoroethyl) pyridin-3-yl)-2-(fluoromethyl)-5-oxo-1,4,5,7-tetrahydrofuro [3,4-b]pyridine-3-carboxylate stereoisomer was found to have a higher activity than its corresponding enantiomer. It is therefore assumed that the $C_{10}$ position on the dihydropyridine ring adopts the same spacial configuration for the most active stereoisomer in each Example.

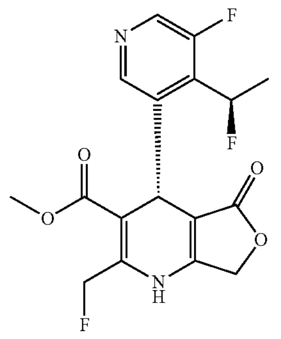 [SMILES: COC(=O)C1=C(CF)NC2=C(C(=O)OC2)[C@H]1c1cncc(F)c1[C@@H](C)F]

methyl (R)-4-(5-fluoro-4-((R)-1-fluoroethyl) pyridin-3-yl)-2-(fluoromethyl)-5-oxo-1,4,5,7-tetrahydrofuro [3,4-b]pyridine-3-carboxylate Example numbers (Example 1, 2, 3, etc.) are given for the active enantiomers which are all assumed to have the same configuration around the $C_{10}$ position on the dihydropyridine ring (examples can be designated either R or S depending upon substitution of the ring system). All other isomers isolated from the synthesis were given example numbers with letters (Example 1b, 2b, 3b etc.). Although there is strong evidence to suggest that the $C_{10}$ position depicted is the desired stereochemistry, there is still the chance that the other configuration could be the active enantiomer in some of the Examples.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR.

All starting materials, building blocks, reagents, acids, bases, dehydrating agents, solvents, and catalysts utilized to synthesis the compounds of the present disclosure are either commercially available or can be produced by organic synthesis methods known to one of ordinary skill in the art. Further, the compounds of the present disclosure can be produced by organic synthesis methods known to one of ordinary skill in the art as shown in the following examples. Abbreviations used are those conventional in the art or the following:

$^1H$ NMR proton nuclear magnetic resonance
AUX auxiliary subunit of $Ca_v1.2$ channel
C Celsius
CD3OD methanol-d4

CDCl3 chloroform-d
CHO Chinese Hamster Ovary cells
Ct threshold cycle in a quantitative polymerase chain reaction assay
d doublet
DAST diethylaminosulfur trifluoride
DCM dichloromethane
dd doublet of doublets
DME 1,4-dimethoxyethane
DMEM Dulbecco's Modified Eagle Medium
DMF N,N-dimethylformamide
DMSO dimethylsulfoxide
DMSO-d6 dimethylsulfoxide-d6
D-PBS Dulbecco's Phosphate Buffered Saline
EC50 Half maximal effective concentration
EDTA Ethylenediaminetetraacetic acid
EGTA Ethylene glycol-bis (β-aminoethyl ether)-N,N,N',N'-tetraacetic acid
Eq. equivalents
EtOAc ethyl acetate
FAM 6-carboxyfluorescein
FCS Furin Cleavage Site
FRT Flippase recognition target site
g gram
h hour(s)
$H_2O$ water
HEPES 4-(2-hydroxyethyl)-1-piperazineethanesulfonic acid
HOBt 1-hydroxy-7-azabenzotriazole
HPLC high pressure liquid chromatography
HRMS high resolution mass spectrometry
Hrs hours
Hz hertz
IACUC Institutional Animal Care and Use Committee
IPA isopropyl alcohol
kg kilogram
L liter
LCMS liquid chromatography mass spectrometry
M molar
m multiplet
m/z mass to charge ratio
mg milligram
MHz mega hertz
min minutes
mL milliliter
ml milliliter
mL/min milliliters per minute
mm millimeter
mM millimolar
mmol millimoles
mRNA messenger ribonucleic acid
MS mass spectrometry
mV millivolt
μl microliter
N normal
n-BuLi n-butyllithium
NMR nuclear magnetic resonance
NOESY nuclear Overhauser effect spectroscopy
pCMV the cytomegalovirus promoter
P2A a peptide self-cleavage sequence derived from porcine teschovirus-1
PdCl2 (dppf) Dichloro [1,1'-bis(diphenylphosphino) ferrocene]palladium (II)
PD Pharmacodynamics
PK Pharmacokinetics
ppm parts per million
PyBOP benzotriazol-1-yloxytripyrrolidinophosphonium hexafluorophosphate
QT the time interval between the Q wave and T wave of an electrocardiogra
rac racemic
rpm round per minute
RNA ribonucleic acid
RT room temperature
Rt retention time
RT-PCR Reverse Transcription-Polymerase Chain Reaction
S singlet
SFC supercritical fluid chromatography
SFM Serum Free Medium
SNP Single Nucleotide Polymorphism
t triplet
TFA trifluoroacetic acid
THF tetrahydrofuran
THF tetrahydrofuran
uL microliter
Um micrometer
UPLC ultra performance liquid chromatography
UV ultraviolet
VIC 2'-chloro-7'phenyl-1,4-dichloro-6-carboxy-fluorescein
v/v volume/volume percent Small Molecule X-Ray Crystallography Data collection Intensity data were collected at 100 K on a Bruker AXS three-circle diffractometer with monochromated Cu(Kα)-radiation, microsource generator, and a Photon III detector using the APEX 3 software (Bruker AXS (2016)). 21 w-scans at different 2θ- and ϕ-positions were performed to ensure appropriate data redundancy (14.9, Friedel pairs not merged). Data processing and global cell refinement were performed with Saint (Bruker AXS (2012)). A semi-empirical absorption correction based on the intensities of symmetry-related reflections measured at different angular settings was applied using SADABS-2016/2 (Krause et al (2015)).

Structure Solution and Refinement

The structure was solved by dual space-recycling methods and subsequent DF syntheses and refined based on full-matrix least-squares on F2 using the SHELXTL program suite (Sheldrick GM (2001)).

Anisotropic displacement parameters were used for all non-hydrogen atoms. Hydrogen atoms were located in DF maps and refined in idealized positions using a riding model.

REFERENCES

Allen FH, Kennard O, Watson D et al (1987) Tables of Bond Lengths determined by X-Ray and Neutron Diffraction. Part 1, Bond Lengths in Organic Compounds. J. Chem. Soc. Perkin Trans II; S1-S19.

Bruker AXS (2005) SMART V5.632. Bruker AXS Inc., Madison, WI, USA.

Bruker AXS (2012) SAINT V7.36A. Bruker AXS Inc., Madison, WI, USA.

Krause L, Herbst-Irmer R, Sheldrick GM et al (2015) Comparison of silver and molybdenum microfocus X-ray sources for single-crystal structure determination. J. Appl. Cryst.; 48:3-10. Spek AL (2003) Single-crystal structure validation with the program PLATON. J. Appl. Cryst.; 36:7-13.

Sheldrick GM (2001) SHELXTL V6.12. Bruker AXS Inc. Madison, WI, USA.

Analytical LCMS Methods:

Method 1: Column: Synergi 2.5 u MAX-RP 100 A Mercury; MOBILE PHASE: 0.1% Formic acid in Water (A)/ACN (B); GRADIENT/(TIME/% B): 0.1/5, 0.5/5, 1.0/95,1.5/95,2.0/5,3.0/5; Flow: 2.0 mL/min, Temp.: 40° C.

Method 2: Method: API 2000; Gradient: Time/% B: 0/30,0.5/30, 1.5/95,2.4/95,2.5/30,3.0/30; Mobile Phase: 0.1% FA in water (A), ACN (B)

Method 3: Column: ZORBAX ECLIPSE XDB C18 1.8 μm, 50*4.6 mm; Mobile Phase: 0.1% Formic acid in water (A)/ACN (B) Gradient Time Vs % B: 0.0/20, 0.25/20, 01.0/95.0, 2.5/95,3.0/20, 4/20

Method 4: Column: Kinetex 2.6 μm, 100 A 30×3 mm; MOBILE PHASE: 0.1% Formic acid in Water (A)/ACN (B); GRADIENT/(TIME/% B): 0.1/20, 0.25/20, 0.75/95, 1.75/95,2.0/20,2.5/20; Flow: 1.0 mL/min, Temp.: 40° C.

Preparative HPLC Methods for Purification:

Method 1: HPLC Column: XBRIDGE-C18 (19.0×150 mm, 5 micron), Mobile phase-A: 0.1% TFA in $H_2O$, B: $CH_3CN$, gradient (Time/% B): 0/20, 2/20, 8/50) Flow rate: [19 mL/min].

Method 2: HPLC Column: ZORBAX ECLIPSE XDB C18 (21.2×150 mm, 5 micron), Mobile phase-A: 0.1% TFA in $H_2O$, B: $CH_3CN$, gradient (Time/% B): 0/10, 2/20, 10/40 and Flow rate: [20 mL/min].

Method 3: HPLC Column: XBRIDGE C18 (21.2×150 mm, 5 micron), Mobile phase-A: 10 mM $NH_4HCO_3$ in water, B: CH3CN, gradient (Time/% B): 0/10, 2/20, 8/50 and Flow rate: [18 mL/min].

Method 4: HPLC Column: Gemini NX C18 (21.2×150.00 mm, 5 micron); Mobile Phase-(A): 0.1% TFA in water (B): Acetonitrile/Methanol; Flow: 15 ml/min; (Time/% B 0/20, 2/20, 8/20)

Method 5: HPLC Column: KINETEX EVO 5 p C18 (21.2×150 mm), Mobile Phase: WATER (A) $CH_3CN$ (B), gradient (Time/% B): 0/20, 2/30, 7/70 and Flow rate: [18 mL/min].

Method 6: HPLC Column: KINETEX C18, (21.2×150 mm), Mobile phases: A: WATER, B: $CH_3CN$: MeOH, gradient (Time/% B): 0/20, 2/30, 7/70, Flow rate: 18 mL/min].

Method 7: HPLC Column: KINETEX (21.2×150 mm, 5 micron), Mobile phases: A=0.05% TFA in water, B=$CH_3CN$, gradient (Time/% B): 0/20, 2/30, 10/60, Flow rate: 20 mL/min].

Chiral Preparative HPLC Methods for Separation of Isomers:

Method 1: Column: CHIRALPAK IC (10×250 mm, 5 micron), Mobile Phase: Hexane (A) IPA: MeOH, 1:1 (B); Flow rate: 8 mL/min; Isocratic: 96:04 (A: B).

Method 2: Column: REGIS WELKO (250×10 mm, 5 micron), Mobile Phase: Hexane (A): EtOH, 1:1 (B); Flow rate: 9 mL/min; Isocratic: 85:15 (A: B).

Method 3: Column: CHIRALPAC IG (250×10 mm, 5 micron), Mobile Phase: IPA (A): MeOH, 1:1 (B); Flow rate: 6 mL/min; Isocratic: 98:2 (A: B).

Method 4: Column: LUX CELLULOSE-4 (10×250 mm, 5 micron), Mobile Phase: Hexane (A) EtOH: IPA 1:1 (B); Flow rate: 8 mL/min; Isocratic: 90: 10 (A: B).

Preparation of Intermediates and General Procedures:

Intermediate A: Formation of ethyl 4-acetoxy-3-oxobutanoate

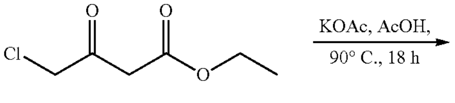

-continued

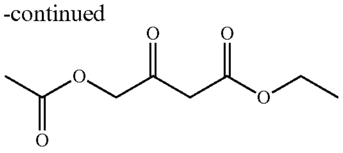

To a solution of ethyl 4-chloro-3-oxobutanoate (200 g, 1215.1 mmol) in acetic acid (1500 mL) was added potassium acetate (357 g, 3645.4 mmol). The resulting solution was stirred at 90° C. for 18 hrs. The solvent was cooled to RT, added to water (2 L) and extracted into ethyl acetate (1 L×4 times). EtOAc phases were combined and washed with saturated $NaHCO_3$ solution (2 L), brine and dried over $Na_2SO_4$. The solvent was removed under reduced pressure and purification of the crude product by silica flash chromatography (0-15%) ethyl acetate in petroleum ether afforded the title compound as a light brown liquid ethyl 4-acetoxy-3-oxobutanoate. $^1H$ NMR (400 MHZ, CDCl3) δ 4.78 (s, 2H), 4.20 (q, J=14.1, 7.2 Hz, 2H), 3.49 (s, 2H), 2.16 (s, 3H), 1.28 (t, J=7.2 Hz, 3H).

Intermediate B: Formation of methyl (Z)-3-amino-4-fluorobut-2-enoate

Method 1:

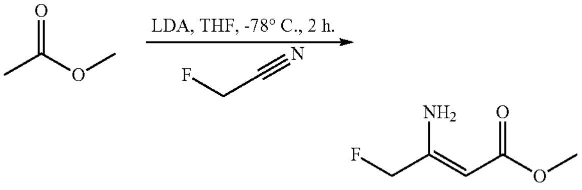

A solution of methyl acetate (36.5 g, 492.71 mmol) in tetrahydrofuran (200 mL) under nitrogen atmosphere was cooled to −78° C., lithium diisopropylamide in THF (246.44 mL, 2.0 M, 492.71 mmol) was added to reaction slowly over a period of 20 min, the resulting mixture was stirred for 1 h at −78° C. followed by addition of 2-fluoroacetonitrile (19.4 g, 328.9 mmol) in a solution of tetrahydrofuran (150 mL) drop wise. Reaction mixture and stirred at −78° C. for another 1 h before addition of saturated ammonium chloride solution (200 mL) was added and product extracted into ethyl acetate (5 L). EtOAc was washed with saturated brine solution (500 mL) and dried over $Na_2SO_4$. The solvent was removed under reduced pressure and purification of the crude product by silica flash chromatography (0-+10%) ethyl acetate in petroleum ether afforded the title compound as a white crystalline solid methyl (Z)-3-amino-4-fluorobut-2-enoate.

Method 2:

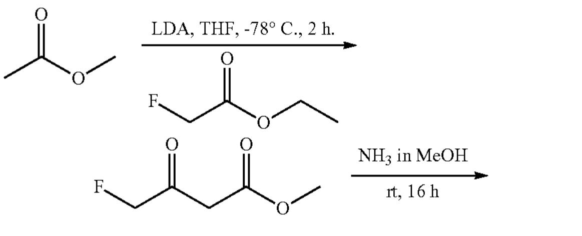

-continued

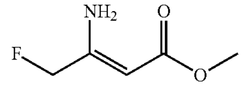

Step 1: A solution of methyl acetate (83.78 g, 1131.0 mmol) in tetrahydrofuran (800 mL) under nitrogen atmosphere was cooled to −78° C., then lithium diisopropylamide in THF (565.5 mL, 2.0 M, 1131.0 mmol) was added to reaction slowly over a period of 20 min. Resulting mixture was stirred for 1 h at −78° C. and then ethyl 2-fluoroacetate (100 g, 942.5 mmol) was added in a solution of tetrahydrofuran (200 mL) drop wise and the reaction mixture and stirred at −78° C. for another 1 h.

Saturated ammonium chloride solution (200 mL) was added to reaction mixture and product extracted into ethyl acetate (5 L). EtOAc was washed with saturated brine solution (500 mL) and dried over $Na_2SO_4$. The solvent was removed under reduced pressure and purification of the crude product by silica flash chromatography (0-10%) ethyl acetate in petroleum ether to give yellow crystals of methyl 4-fluoro-3-oxobutanoate. $^1H$ NMR (400 MHZ, CDC13) δ 4.97 (s, 1H), 4.85 (s, 1H), 3.76 (d, J=2.3 Hz, 3H), 3.62 (d, J=3.7 Hz, 2H).

Step 2: To methyl 4-fluoro-3-oxobutanoate (from step 1, 60 g) in a sealed tube was added saturated ammonia solution in methanol (300 mL) at room temperature. The resulting mixture was stirred at room temperature for 16 hrs. The solvent was removed under reduced pressure afforded the title compound as a white solid methyl (Z)-3-amino-4-fluorobut-2-enoate. $^1H$ NMR (300 MHZ, DMSO-d6) δ 4.98 (t, J=0.7, 0.7 Hz, 1H), 4.82 (t, J=0.7, 0.7 Hz, 1H), 4.53 (q, 1H), 3.53 (d, J=1.2 Hz, 3H).

Intermediate C: methyl (Z)-3-amino-4,4-dimethoxybut-2-enoate

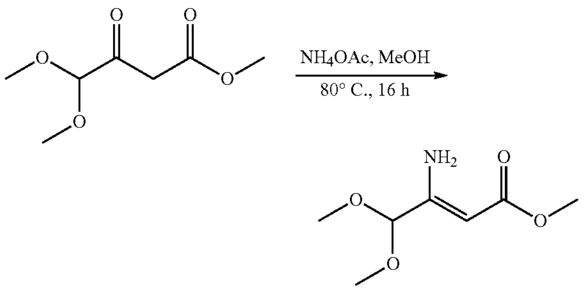

To a stirred solution of methyl 4,4-dimethoxy-3-oxobutanoate (2.00 g, 11.35 mmol) in MeOH (20.00 mL), was added $NH_4OAc$ (4.37 g, 56.76 mmol) at RT and the reaction mixture was heated to 80° C. for 16 h. The solvent was removed under reduced pressure and residue was diluted with DCM (15 mL), filtered over celite and celite cake washed with DCM (3×15 mL). The filtrate was concentrated under reduced pressure to afford title compound as dark wine red color syrup. methyl (Z)-3-amino-4,4-dimethoxybut-2-enoate. $^1H$ NMR (300 MHZ, CDC13) 4.80-4.79 (m, 2H), 3.66 (s, 3H), 3.34 (s, 6H)

General Procedure I

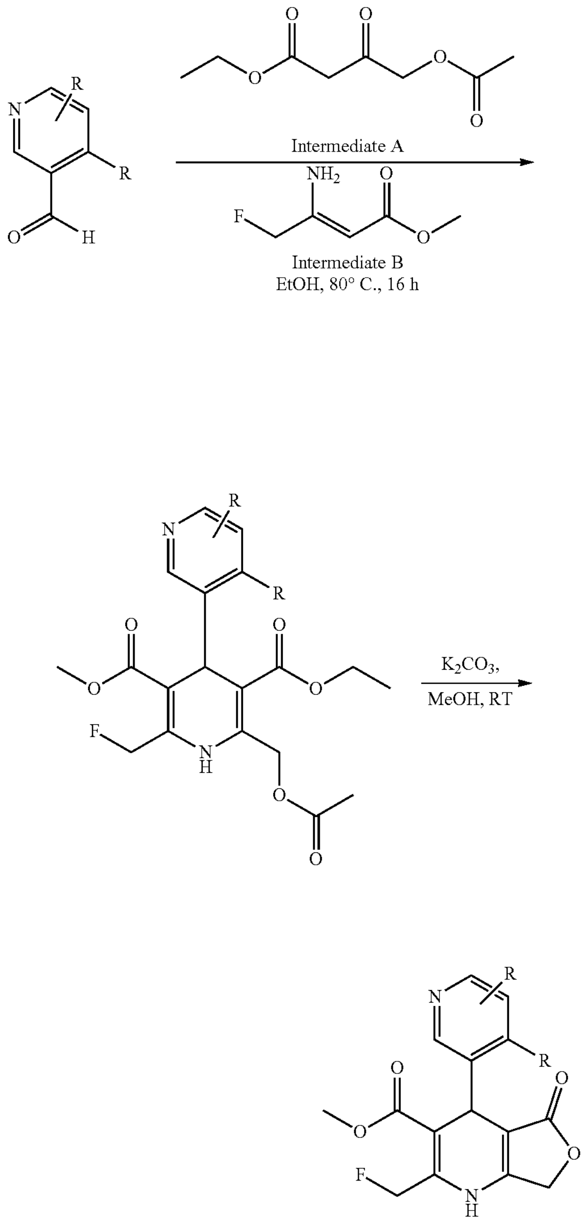

Step 1: To a solution of aldehyde (1 eq.) in EtOH (0.2M) was added methyl (Z)-3-amino-4-fluorobut-2-enoate (intermediate B, 1 or 1.2 eq.) and ethyl 4-acetoxy-3-oxobutanoate (intermediate A, 1 or 1.2 eq.). The resulting solution was stirred at 80° C. for 16 hrs. The solvent was removed under reduced pressure afforded the title compound (crude).

Step 2: To a crude intermediate from step 1 in methanol (10 mL) was added potassium carbonate (5 mmol). The resulting solution was stirred at room temperature for 2 hrs. The solvent was removed under reduced pressure and added to water. Product was extracted into ethyl acetate, washed with brine and dried over $Na_2SO_4$. The solvent was removed under reduced pressure and purification of the crude product was carried out by silica flash chromatography.

General procedure II: Formation of 2-methyl-5-oxo-1,4,5,7-tetrahydrofuro [3,4-b]pyridine-3-carboxylate compounds

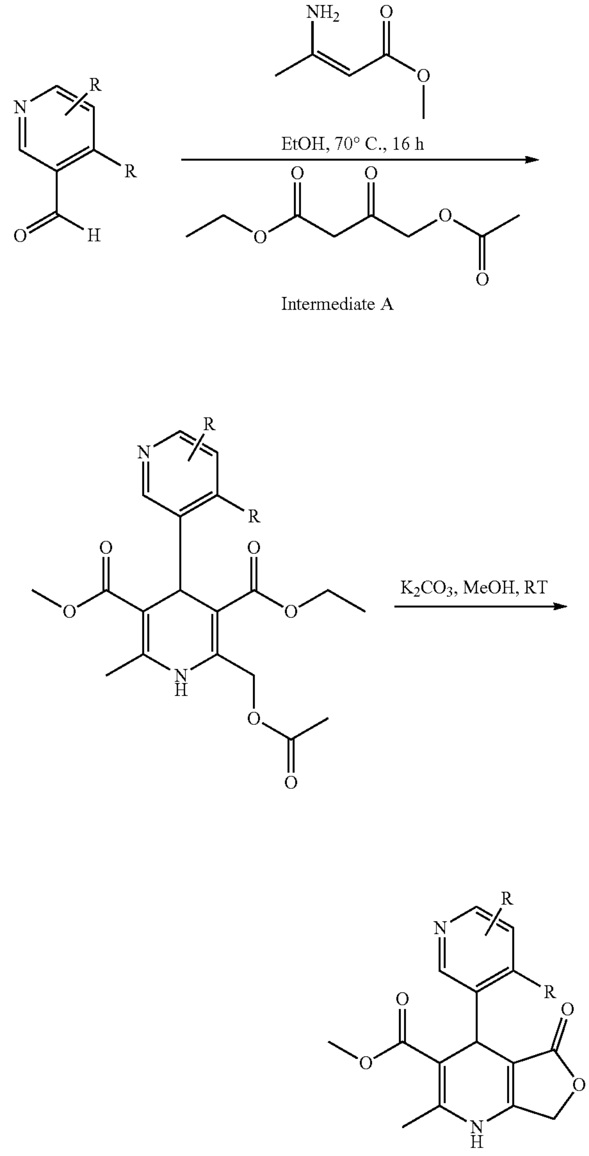

Step 1: To a solution of aldehyde (1 eq.) and methyl (Z)-3-aminobut-2-enoate (1 eq.) in EtOH or MeOH (0.3M) was added ethyl 4-acetoxy-3-oxobutanoate (Intermediate A, 1 eq.). The resulting solution was stirred at 80° C. for 14 hrs. The solvent was removed under reduced pressure and afforded the crude compound that was generally taken onto step two without further purification.

Step 2: To a crude intermediate from step 2 in methanol (0.3M) was added potassium carbonate (3 eq.). The resulting solution was stirred at room temperature for 2 hrs. The solvent was removed under reduced pressure, added to water (500 mL), extracted into ethyl acetate and dried over $Na_2SO_4$. The solvent was removed under reduced pressure and purification of the crude product by silica flash chromatography afforded the product.

Example 1: methyl(S)-4-(5-fluoro-4-((R)-1-fluoroethyl) pyridin-3-yl)-2-methyl-5-oxo-1,4,5,7-tetrahydrofuro [3,4-b] pyridine-3-carboxylate or methyl(S)-4-(5-fluoro-4-((S)-1-fluoroethyl) pyridin-3-yl)-2-methyl-5-oxo-1,4,5,7-tetrahydrofuro [3,4-b]pyridine-3-carboxylate

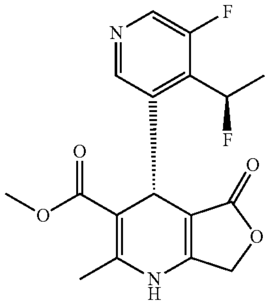

or

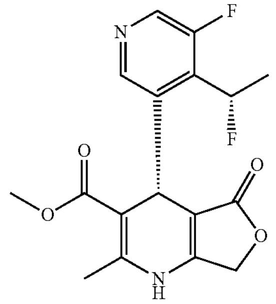

Step 1:1-(3-bromo-5-fluoropyridin-4-yl) ethan-1-ol

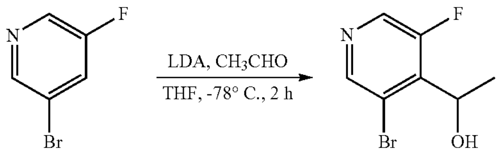

To a cooled stirring solution of 3-bromo-5-fluoropyridine (10 g, 56.82 mmol) in THF (100 mL) at −78° C., was added LDA (2M in THF) (34.09 mL, 68.18 mmol). Reaction was stirred for 1 h then $CH_3CHO$ (9.56 mL, 170.46 mmol) was at −78° C. and the reaction mixture was stirred at same temperature for 1 h. Reaction mixture was poured into 10% ammonium chloride solution and product extracted into EtOAc. The combined organic layers were washed with brine, dried over anhydrous $Na_2SO_4$, filtered and the solvent removed under reduced pressure. The crude product was purified by silica flash chromatography (20%) ethyl acetate in hexane to afford the title compound as pale orange color liquid. 1-(3-bromo-5-fluoropyridin-4-yl) ethan-1-ol. LCMS: Rt=0.248 min; MS m/z 219.8 [M+H]+; [Method 1]. $^1$H NMR (400 MHZ, CDCl3) δ 8.50 (s, 1H), 8.36 (d, J=1.2 Hz, 1H), 5.32-5.28 (m, 1H), 2.61-2.59 (m, 1H), 1.62 (d, J=6.4 Hz, 3H).

Step 2:3-bromo-5-fluoro-4-(1-fluoroethyl) pyridine

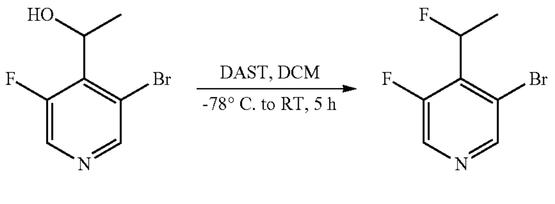

To a cooled stirring solution of 1-(3-bromo-5-fluoropyridin-4-yl) ethan-1-ol (from step 1, 11.5 g, 52.26 mmol) in DCM (100 mL) at −78° C., was added DAST (8.3 mL, 62.71 mmol) dropwise. The reaction mixture was allowed to warm to RT stirred for 5 h. The reaction mixture was quenched with ice water and product extracted into DCM. The combined organic layers were washed with 10% $NaHCO_3$ solution, brine, dried over anhydrous $Na_2SO_4$, filtered and solvent removed under reduced pressure at 30° C. The crude product was purified by silica flash chromatography (7% ethyl acetate in hexane) to afford the title compound as pale yellow liquid. 3-bromo-5-fluoro-4-(1-fluoroethyl) pyridine. LCMS: Rt=1.154 min; MS m/z 223.8 [M+H]+; [Method 2]. $^1$H NMR (400 MHZ, CDCl3) δ 8.55 (s, 1H), 8.42 (s, 1H), 6.10-5.92 (m, 1H), 1.74 (dd, J=22.8, 6.4 Hz, 3H).

Step 3:3-fluoro-4-(1-fluoroethyl)-5-vinylpyridine

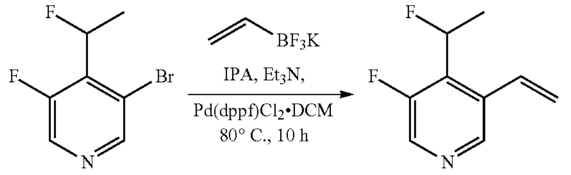

To a stirred solution 3-bromo-5-fluoro-4-(1-fluoroethyl) pyridine (from step 2, 8.3 g, 37.38 mmol) in IPA (80.00 mL), was added potassium vinyltrifluoroborate (10.01 g, 74.76 mmol) followed by Et3N (20.8 mL, 149.5 mmol) at RT and reaction purged with argon gas for 10 minutes. Pd (dppf) Cl2.DCM (1.53 g, 1.869 mmol) was added at RT and reaction purged with argon gas for another 5 minutes. Reaction mixture was heated to 80° C. for 10 h. Solvent removed under reduced pressure. The crude product was purified by silica flash chromatography (7% ethyl acetate in hexane) to afford the title compound a pale yellow liquid. 3-fluoro-4-(1-fluoroethyl)-5-vinylpyridine. LCMS: Rt=0.935 min; MS m/z 170.1 [M+H]+; [Method 2]. $^1$H NMR (400 MHz, $CDCl_3$) δ 8.52 (s, 1H), 8.36 (s, 1H), 7.07 (dd, J=17.6, 11.6 Hz, 1H), 6.12-5.92 (m, 1H), 5.71 (d, J=17.6 Hz, 1H), 5.49 (d, J=11.2 Hz, 1H), 1.70 (dd, J=23.2, 6.8 Hz, 3H).

Step 4:5-fluoro-4-(1-fluoroethyl) nicotinaldehyde

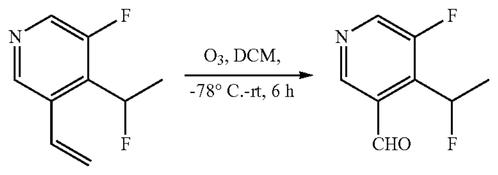

To a cooled stirring solution of 3-fluoro-4-(1-fluoroethyl)-5-vinylpyridine (from step 3, 3.8 g, 22.46 mmol) in DCM (250 mL) at −78° C. was purged with O3 slowly for 6 h. After completion of the reaction, it was quenched with DMS (2.49 ml, 33.69 mmol) and the reaction mixture was stirred for 20 min. Ice cold water was added and product extracted into DCM. Combined organic layers were washed with brine, dried over anhydrous $Na_2SO_4$, filtered and solvent removed under reduced pressure at 30° C. to get the title compound as pale orange liquid. 5-fluoro-4-(1-fluoroethyl) nicotinaldehyde. LCMS: Rt=1.406 min; MS m/z 172.2 [M+H]+; [Method 1]. $^1$H NMR (400 MHZ, CDCl3) δ 10.43 (s, 1H), 8.84 (s, 1H), 8.63 (s, 1H), 6.48-6.30 (m, 1H), 1.80 (dd, J=23.2, 6.6 Hz, 3H).

Step 5 & 6: methyl 4-(5-fluoro-4-(1-fluoroethyl) pyridin-3-yl)-2-methyl-5-oxo-1,4,5,7-tetrahydrofuro [3,4-b]pyridine-3-carboxylate

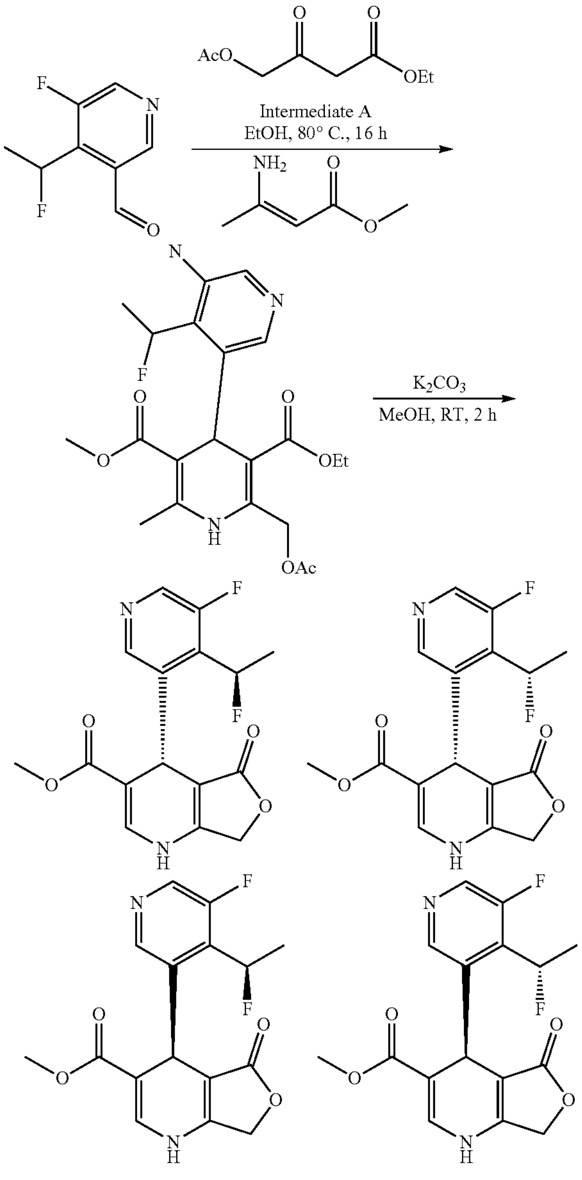

The title compound was synthesized using general method II (using aldehyde from step 4, 2 g, 11.68 mmol). The crude product was purified by silica flash chromatography (60% ethyl acetate in hexane) to afford the title compound as brown solid (1.7 g). Diastereomers were separated by Prep HPLC (Column: WATERS×BRIDGE (150 mm×20.0 mm), 5.0 μ; Mobile Phase: A=WATER, B=ACN; Flow: 15 ml/min) to afford rac-diastereomer 1 and rac-diastereomer 2. The absolute stereochemistry of the four stereoisomers corresponding to the four product peaks was not determined.

First eluting isomer rac-diastereomer 1 was separated into its enantiomers by chiral HPLC (Column: REGIS WHELK, 250 MM×21.2 MM×5 MICRON; Mobile Phase: HEXANE (A), EtOH: MeOH, 1:1 (B), FLOW: 15 mL/Min).

Second eluting isomer rac-diastereomer 2 was separated into its enantiomers by chiral HPLC (COLUMN: LUX AMYLOSE-2, 250 MM×21.2 MM×5 MICRON; MOBILE PHASE: HEXANE (A), EtOH: MeOH, 1:1 (B); FLOW: 15 mL/Min).

Example 1 is the second eluting enantiomer of rac-diastereomer 2

Chiral HPLC Rt=6.19 min (Column: I CELLUYLOSE-C(250×4.6 mm, 5 micron); Mobile Phase: A: n-Hexane, B=IPA: MEOH (50:50); Flow: 1.0 ml/min).

LCMS: Rt=0.653 min; MS m/z 351.0 [M+H]+; [Method 2]

$^{1}$H NMR (400 MHZ, DMSO-d6) δ 10.01 (s, 1H), 8.38 (d, J=2.4 Hz, 1H), 8.30 (s, 1H), 6.43-6.26 (m, 1H), 5.00 (s, 1H), 4.88 (d, J=25.6, 16.4 Hz, 2H), 3.44 (s, 3H), 2.33 (s, 3H), 1.80 (dd, J=23.6, 6.4 Hz, 3H).

Example 1a: First eluting enantiomer of rac-diastereomer 2

Chiral HPLC Rt=5.775 min (Column: I CELLUYLOSE-C(250×4.6 mm, 5 micron); Mobile Phase: A: n-Hexane, B=IPA: MEOH (50:50); Flow: 1.0 ml/min).

LCMS: Rt=0.615 min; MS m/z 351.0 [M+H]+; [Method 2].

$^{1}$H NMR (400 MHZ, DMSO-d6) Õ 10.01 (s, 1H), 8.38 (d, J=2.4 Hz, 1H), 8.30 (s, 1H), 6.43-6.26 (m, 1H), 5.00 (s, 1H), 4.88 (d, J=25.6, 16.4 Hz, 2H), 3.44 (s, 3H), 2.33 (s, 3H), 1.80 (dd, J=23.6, 6.4 Hz, 3H).

Example 1b: First eluting enantiomer of rac-diastereomer 1

Chiral HPLC Rt=2.367 min (Column: LUX, AMYLOSE-1 (150×4.6 mm, 5 Micron); Mobile Phase: A: n-HEXANE, B=0.1% DEA IN ETHANOL: METHANOL (70:30); Flow: 1.0 ml/min).

LCMS: Rt=0.50 min; MS m/z 351.0 [M+H]+; [Method 2].

$^{1}$H NMR (400 MHZ, DMSO-d6) Õ 10.03 (s, 1H), 8.39 (d, J=2.8 Hz, 1H), 8.24 (s, 1H), 6.58-6.42 (m, 1H), 4.96 (s, 1H), 4.86 (d, J=25.6, 16.4 Hz, 2H), 3.45 (s, 3H), 2.36 (s, 3H), 1.72 (dd, J=23.6, 6.8 Hz, 3H).

Example 1c: Second eluting enantiomer of rac-diastereomer 1

Chiral HPLC Rt=2.765 min (Column: LUX, AMYLOSE-1 (150×4.6 mm, 5 Micron); Mobile Phase: A: n-HEXANE, B=0.1% DEA IN ETHANOL: METHANOL (70:30); Flow: 1.0 ml/min).

LCMS: Rt=0.498 min; MS m/z 351.2 [M+H]+; [Method 2].

$^{1}$H NMR (400 MHZ, DMSO-d6) δ 10.03 (s, 1H), 8.39 (d, J=2.8 Hz, 1H), 8.24 (s, 1H), 6.58-6.42 (m, 1H), 4.96 (s, 1H), 4.86 (d, J=25.6, 16.4 Hz, 2H), 3.45 (s, 3H), 2.36 (s, 3H), 1.72 (dd, J=23.6, 6.8 Hz, 3H).

Example 2: methyl (R)-4-(5-fluoro-4-((R)-1-fluoroethyl) pyridin-3-yl)-2-(fluoromethyl)-5-oxo-1,4,5,7-tetrahydrofuro [3,4-b]pyridine-3-carboxylate

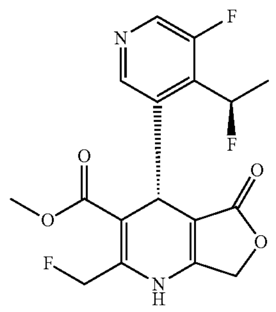 [SMILES: COC(=O)C1=C(CF)NC2=C(C(=O)OC2)[C@H]1c1cncc(F)c1[C@@H](C)F]

Step 1 & 2: methyl 4-(5-fluoro-4-(1-fluoroethyl) pyridin-3-yl)-2-(fluoromethyl)-5-oxo-1,4,5,7-tetrahydrofuro [3,4-b]pyridine-3-carboxylate

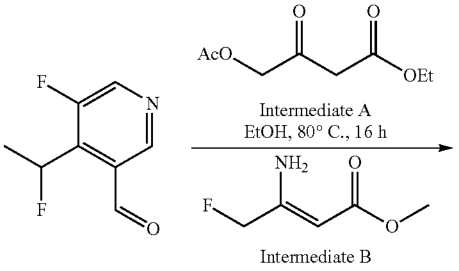

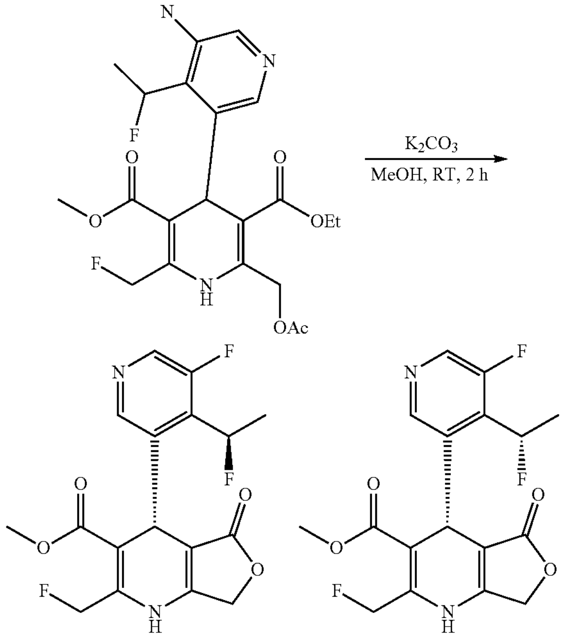

-continued

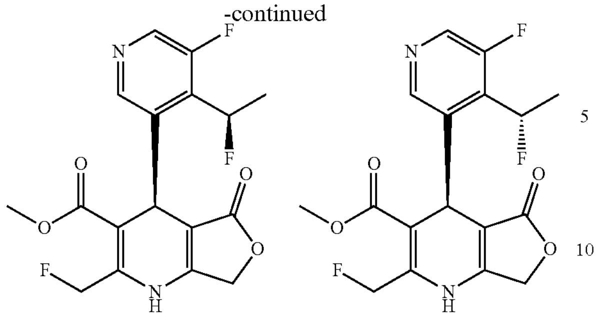

The title compound was synthesized using general method I (using aldehyde from example 1, step 4, 1.8 g, 10.52 mmol). Crude product was purified silica flash chromatography (5% MeOH in CHCl3) to afford the title compound. Diastereomers were separated by Prep HPLC (Column: LUNA C18 (250 mmx 21.2 mm), 5.0 μ; Mobile Phase: A: 0.1% HCOOH: B: Acetonitrile; Flow Isocratic: 20 mL/min) to afford rac-diastereomer 1 and rac-diastereomer 2.

rac-diastereomer 1 was separated into its enantiomers by chiral HPLC (Column: REGIS WHELK, 250 MM×21.2 MM×5 MICRON; Mobile Phase: A: Hexane: B: EtOH: MeOH: 1:1, FLOW: 15 mL/Min).

rac-diastereomer 2 was separated into its enantiomers by chiral HPLC (Column: REGIS WHELK, 250 MM×21.2 MM×5 MICRON; Mobile Phase: A: Hexane: B: EtOH: MeOH: 1:1, FLOW: 15 mL/Min).

Example 2 is the first eluting enantiomer of rac-diastereoisomer 2

Chiral HPLC Rt=5.086 min (Regis, (S, S) Whelk-01-(150×4.60 mm, 5 micron); Mobile Phase: A=n-HEXANE, B=0.1% DEA in ETHANOL: METHANOL (70:30)).

The absolute stereochemistry of Example 2, methyl (R)-4-(5-fluoro-4-((R)-1-fluoroethyl) pyridin-3-yl)-2-(fluoromethyl)-5-oxo-1,4,5,7-tetrahydrofuro [3,4-b]pyridine-3-carboxylate, was determined by single crystal x-ray crystallographic analysis (FIG. 2).

LCMS: Rt=0.723 min; MS m/z 369.1 [M+H]+; [Method 2].

$^1$H NMR (400 MHZ, DMSO-d6) δ 10.25 (s, 1H), 8.39 (d, J=1.8 Hz, 1H), 8.34 (s, 1H), 6.47-6.23 (m, 1H), 5.68 (s, 1H), 5.56 (s, 1H), 5.06 (s, 1H), 4.84 (dd, J=30.0, 16.8 Hz, 2H), 3.43 (s, 3H), 1.80 (dd, J=23.6, 6.8 Hz, 3H).

Example 2a: Second eluting enantiomer of rac-diastereoisomer 2

Chiral HPLC Rt=5.702 min (Regis, (S, S) Whelk-01-(150×4.60 mm, 5 micron); Mobile Phase: A=n-HEXANE, B=0.1% DEA in ETHANOL: METHANOL (70:30)).

LCMS: Rt=0.742 min; MS m/z 369.1 [M+H]+; [Method 2].

$^1$H NMR (400 MHZ, DMSO-d6) δ 10.23 (brs, 1H), 8.38 (d, J=2.2 Hz, 1H), 8.34 (s, 1H), 6.48-6.26 (m, 1H), 5.67 (s, 1H), 5.55 (s, 1H), 5.05 (s, 1H), 4.95-4.74 (m, 2H), 3.43 (s, 3H), 1.80 (dd, J=23.2, 6.0 Hz, 3H)

Example 2b: First eluting enantiomer of rac-diastereoisomer 1

Chiral HPLC Rt=5.949 min (Regis, (S, S) Whelk-01-(150×4.60 mm, 5 micron); Mobile Phase: A=n-HEXANE, B=0.1% DEA in ETHANOL: METHANOL (70:30)).

LCMS: Rt=0.576 min; MS m/z 369.1 [M+H]+; [Method 2].

$^1$H NMR (400 MHZ, DMSO-d6) δ 10.23 (s, 1H), 8.39 (d, J=2.7 Hz, 1H), 8.29 (s, 1H), 6.64-6.32 (m, 1H), 5.75 (s, 1H), 4.60 (s, 1H), 5.00 (s, 1H), 4.92-4.75 (m, 2H), 3.43 (s, 3H), 1.69 (dd, J=23.7, 6.6 Hz, 3H).

Example 2c: Second eluting enantiomer of rac-diastereoisomer 1

Chiral HPLC Rt=8.470 min (Regis, (S, S) Whelk-01-(150×4.60 mm, 5 micron); Mobile Phase: A=n-HEXANE, B=0.1% DEA in ETHANOL: METHANOL (70:30)).

LCMS: Rt=0.584 min; MS m/z 369.2 [M+H]+; [Method 2].

$^1$H NMR (400 MHZ, DMSO-d6) δ 10.26 (s, 1H), 8.41 (s, 1H), 8.31 (s, 1H), 6.61-6.41 (m, 1H), 5.75 (s, 1H), 4.63 (s, 1H), 5.02 (s, 1H), 4.94-4.79 (s, 2H), 3.44 (s, 3H), 1.72 (dd, J=23.2, 6.6 Hz, 3H).

Example 3: methyl (R)-4-(4-ethyl-5-fluoropyridin-3-yl)-2-(fluoromethyl)-5-oxo-1,4,5,7-tetrahydrofuro [3,4-b]pyridine-3-carboxylate

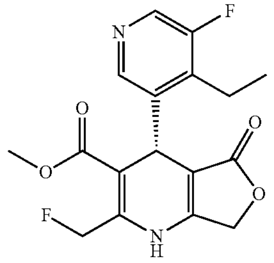 [SMILES: CCc1c(F)cncc1[C@H]1C(C(=O)OC)=C(CF)NC2=C1C(=O)OC2]

Step 1:3-bromo-4-ethyl-5-fluoropyridine

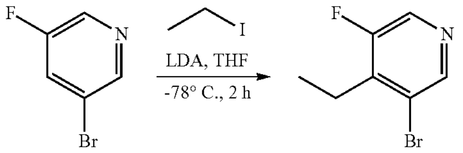

A stirring solution of 3-bromo-5-fluoropyridine (5.0 g, 28.41 mmol) in THF (60.0 mL) was cooled to −78° C. and stirred for 10 min. Lithium diisopropylamide (2M in THF) (21.30 mL, 42.61 mmol) was added dropwise at −78° C. and the reaction mixture was stirred at same temperature for 0.5 h. Iodoethane (2.51 mL, 31.25 mmmol) was added at −78° C. and the reaction mixture was allowed to warm to RT at stirred at room temperature for 2 h. Reaction mixture was quenched by saturated solution of ammonium chloride, diluted with water and product extracted into ethyl acetate. The combined organic layers were washed with saturated brine solution, dried over anhydrous sodium sulfate, filtered, and the solvent removed under reduced pressure. The crude compound was purified by silica flash chromatography (5-6%) ethyl acetate in hexane afforded the title compound as yellow liquid. 3-bromo-4-ethyl-5-fluoropyridine. $^1$H NMR (300 MHZ, CDCl3) δ 8.48 (d, J=3.0 Hz, 1H), 8.30 (s, 1H), 2.83 (dq, J=7.8, 1.8 Hz, 2H), 1.20 (t, J=7.8 Hz, 3H).

Step 2:4-ethyl-5-fluoronicotinaldehyde

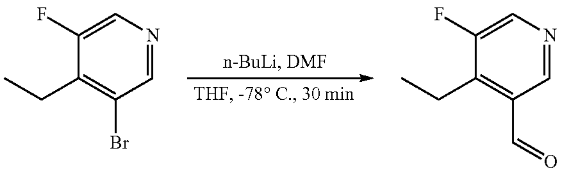

A stirred solution of 3-bromo-4-ethyl-5-fluoropyridine (from step 1, 1.75 g, 8.576 mmol) in THF (20.0 mL), was cooled to −78° C., then n-Butyl lithium (1.6 M in THF) (8.04 mL, 12.86 mmol) was added dropwise at −78° C. and stirred for 10 min. N, N-Dimethylformamide (0.66 mL, 8.576 mmol) was added at −78° C. and the reaction mixture was stirred at same temperature for 20 min. Reaction mixture was quenched with saturated solution of ammonium chloride at −78° C., diluted with water and product extracted into ethyl acetate. The combined organic layers were washed with saturated brine solution, dried over anhydrous sodium sulfate, filtered and the solvent removed under reduced pressure. The crude compound was purified by silica flash chromatography (8-10%) ethyl acetate in hexane afforded the title compound as yellow liquid. 4-ethyl-5-fluoronicotinaldehyde. $^1$H NMR (300 MHZ, DMSO-d6) δ 10.28 (s, 1H) 8.85 (s, 1H), 8.77 (d, J=1.5 Hz, 1H), 3.04 (q, J=7.5 Hz, 2H), 1.17 (t, J=7.2 Hz, 3H).

Step 3 & 4: methyl 4-(4-ethyl-5-fluoropyridin-3-yl)-2-(fluoromethyl)-5-oxo-1,4,5,7-tetrahydrofuro [3,4-b]pyridine-3-carboxylate

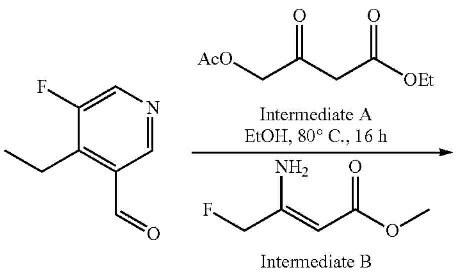

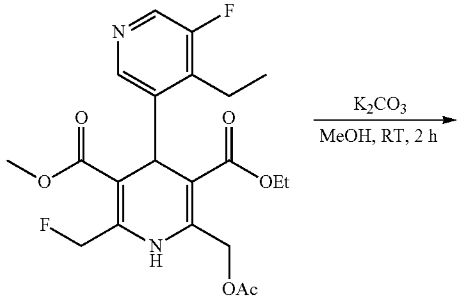

-continued

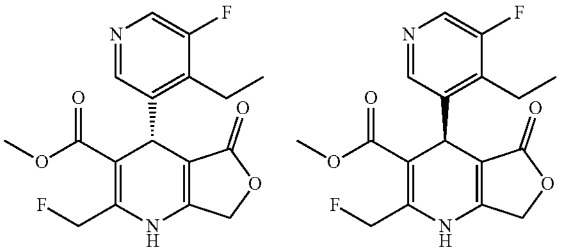

The title compound was synthesized using general method I (using aldehyde from step 2, 0.2 g, 1.31 mmol). Crude product was purified by Prep HPLC to afford the title compound methyl 4-(4-ethyl-5-fluoropyridin-3-yl)-2-(fluoromethyl)-5-oxo-1,4,5,7-tetrahydrofuro [3,4-b]pyridine-3-carboxylate. LCMS Rt=1.403 min; MS m/z 350.75 [M+H]+; [Method 10].

The racemic sample was separated into its enantiomers by chiral HPLC (Column: REGIS WHELK-01, (250 MM×21.1 MM×5 MICRON); Mobile Phase: N-HEXANE (A) EtOH: MeOH, 1: 1 (B), FLOW: 15 ML). The absolute stereochemistry of the two enantiomers corresponding to the two product peaks was not determined.

Peak 1: Chiral HPLC Rt=4.963 min (Column: CHIRAL PAK-IG (150×4.6mm×5 μ); Mobile Phase: A=n-HEXANE, B=0.1% DEA in ETHANOL: METHANOL (70:30); Flow: 1.0 ml/min).

LCMS: Rt=1.388 min; MS m/z 351.0 [M+H]+; [Method 1].

$^1$H NMR (300 MHz, $CDCl_3$) Õ 8.20 (s, 2H), 7.28 (brs, 1H), 5.81 (s, 1H), 5.65 (s, 1H), 5.11 (s, 1H), 4.80 (s, 2H), 3.56 (s, 3H), 3.14-2.96 (m, 2H), 1.33 (t, J=7.5 Hz, 3H).

Peak 2: Chiral HPLC Rt=8.881 min (Column: CHIRAL PAK-IG (150×4.6mm×5 μ); Mobile Phase: A=n-HEXANE, B=0.1% DEA in ETHANOL: METHANOL (70:30); Flow: 1.0 ml/min).

LCMS: Rt=1.386 min; MS m/z 351.1 [M+H]+; [Method 1].

$^1$H NMR (300 MHZ, CDCl3) δ 8.20 (s, 2H), 7.28 (brs, 1H), 5.81 (s, 1H), 5.65 (s, 1H), 5.11 (s, 1H), 4.80 (s, 2H), 3.56 (s, 3H), 3.14-2.96 (m, 2H), 1.33 (t, J=7.8 Hz, 3H).

Example 4: methyl(S)-4-(4-ethyl-5-fluoropyridin-3-yl)-2-methyl-5-oxo-1,4,5,7-tetrahydrofuro [3,4-b] pyridine-3-carboxylate

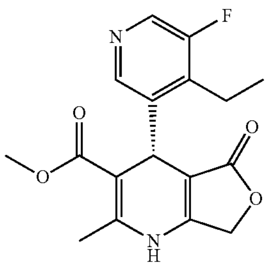 [SMILES: CCc1c(F)cncc1[C@H]1C(C(=O)OC)=C(C)NC2=C1C(=O)OC2]

Step 1 & 2: methyl 4-(4-ethyl-5-fluoropyridin-3-yl)-2-methyl-5-oxo-1,4,5,7-tetrahydrofuro [3,4-b] pyridine-3-carboxylate

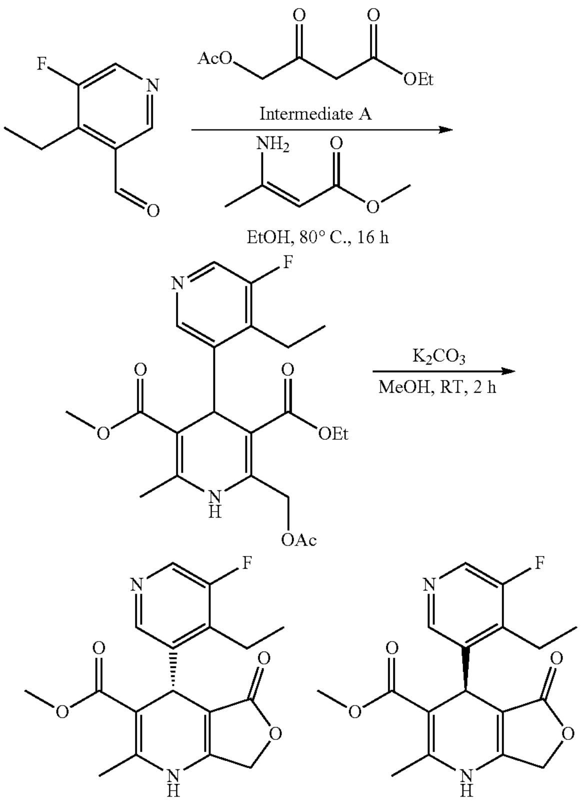

The title compound was synthesized using general method II (using aldehyde from example 3 step 2, 0.2 g, 1.31 mmol). Crude product was purified by Prep HPLC to afford the title compound. LCMS: Rt=1.375 min; MS m/z 332.75 [M+H]+; [Method 1].

The racemic sample was separated into its enantiomers by chiral HPLC (Column: REGIS WHELK-01, (250 MM×21.1 MM×5 MICRON); Mobile Phase: N-HEXANE (A) EtOH: MeOH, 1:1 (B), FLOW: 15 ML/Min). The absolute stereochemistry of the two enantiomers corresponding to the two product peaks was not determined.

Peak 1: Chiral HPLC Rt=3.639 min (Column: LUX-AMYLOSE-2 (150×4.6mm×5 μ)); Mobile Phase: A: n-Hexane, B: 0.1% TFA IN ETHANOL: METHANOL (80:20); Flow: 1.0 ml/min).

LCMS Rt=1.375 min; MS m/z 332.75 [M+H]+; [Method 1].

$^1$H NMR (300 MHZ, DMSO-d6) δ 10.0 (brs, 1H), 8.24 (s, 1H), 8.16 (s, 1H), 4.96 (s, 1H), 4.79-4.76 (m, 2H), 3.43 (s, 3H), 3.08-2.81 (m, 2H), 2.31 (s, 3H), 1.22 (t, J=7.4 Hz, 3H).

Peak 2: Chiral HPLC Rt=4.78 min (Column: LUX-AMYLOSE-2 (150×4.6mm×5 μ)); Mobile Phase: A: n-Hexane, B: 0.1% TFA IN ETHANOL: METHANOL (80:20); Flow: 1.0 ml/min).

LCMS: Rt=1.374 min; MS m/z 330.8 [M−H]−; [Method 1].

$^1$H NMR (400 MHZ, DMSO-d6) δ 10.0 (brs, 1H), 8.23 (s, 1H), 8.15 (s, 1H), 4.95 (s, 1H), 4.78 (dd, J=28.0, 16.4 Hz, 2H), 3.42 (s, 3H), 3.08-2.81 (m, 2H), 2.31 (s, 3H), 1.22 (t, J=7.4 Hz, 3H).

Example 5: methyl (R)-4-(4-ethylpyridin-3-yl)-2-(fluoromethyl)-5-oxo-1,4,5,7-tetrahydrofuro [3,4-b] pyridine-3-carboxylate

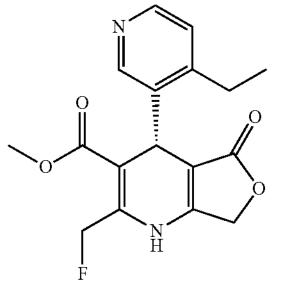 [SMILES: CCc1ccncc1[C@H]1C(C(=O)OC)=C(CF)NC2=C1C(=O)OC2]

Step 1:3-bromo-4-ethylpyridine

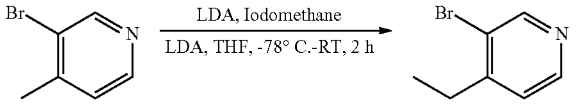

To a stirred solution of 3-bromo-4-methylpyridine (2.0 g, 11.62 mmol), in THF (20 mL), was cooled to −78° C., lithium isopropyl amide (2 M) in THF (6.97 mL, 13.95 mmol) was added and the reaction mixture was stirred at same temperature for 1 h. Then iodomethane (1.98 g, 13.95 mmol) was added and the reaction mixture was stirred for 1 h at RT. Reaction mixture was quenched by using ammonium chloride solution and extracted with ethyl acetate (2×100 mL). The combined organic layers were washed with brine, dried over anhydrous $Na_2SO_4$, and the solvent removed under reduced pressure. The crude product was purified by silica flash chromatography (4-6% ethyl acetate in hexane) to get the desired product as pale-yellow liquid. 3-bromo-4-ethylpyridine. $^1$H NMR (300 MHz, CDCl3) δ 8.64 (s, 1H), 8.41 (d, J=5.0 Hz, 1H), 7.17 (d, J=4.7 Hz, 1H), 2.75 (q, J=7.6 Hz, 2 H), 1.25 (t, J=7.5 Hz, 3H).

Step 2:4-ethylnicotinaldehyde

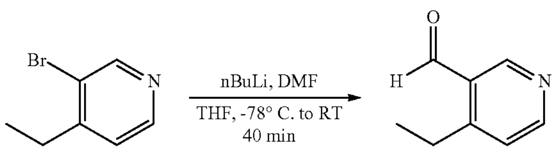

To a cooled stirring solution of 3-bromo-4-ethylpyridine (from step 1, 1.0 g, 5.37 mmol) in THF (10 mL) at −78° C. was added n-Butyl lithium solution (1.6 M) in hexane (4.03 mL, 6.45 mmol). Reaction mixture was stirred for 25 min at same temperature. Then dimethylformamide (0.5 mL, 6.45 mmol) was added and the reaction mixture was stirred for 15 min at room temperature. Reaction was quenched by using ammonium chloride solution and extracted with ethyl acetate (2×50 mL). The combined organic layer was washed with brine, dried over anhydrous $Na_2SO_4$, and the solvent removed under reduced pressure. The crude product was purified by silica flash chromatography (4-6% ethyl acetate in hexane) to obtain the desired product 4-ethylnicotinaldehyde as a pale-yellow liquid. $^1H$ NMR (300 MHZ, CDCl3) δ 10.29 (s, 1H), 8.94 (s, 1H), 8.67 (d, J=5.2 Hz, 1H), 7.27-7.26 (m, 1H, merged with CDCl3), 3.09 (q, J=7.3 Hz, 2H), 1.28 (t, J=7.6 Hz, 3H).

Step 3 & 4: methyl 4-(4-ethylpyridin-3-yl)-2-(fluoromethyl)-5-oxo-1,4,5,7-tetrahydrofuro [3,4-b]pyridine-3-carboxylate

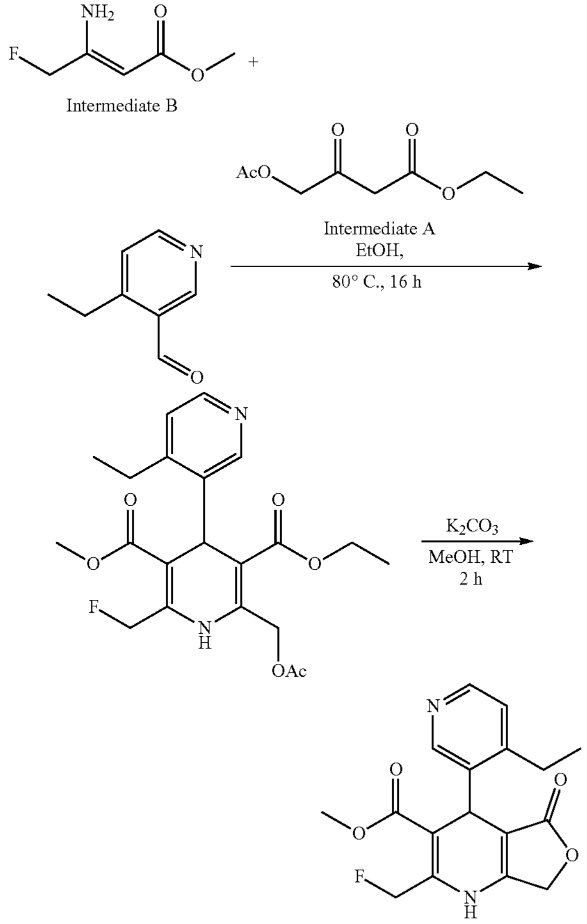

The title compound was synthesized using general method I (using aldehyde from step 2, 0.1 g, 0.74 mmol). Crude product was purified silica flash chromatography (58-60% EtOAc in hexane) to afford the title compound as an off white solid. LCMS: Rt=0.268 min; MS m/z 333.0 [M+H]+; [Method 4]. The racemic compound was separated into its enantiomers by chiral HPLC (Column: REGIS (S, S) WHELK-01,250 MM×21.1 MM×5 MICRON); Mobile Phase: N-HEXANE (A) EtOH: MeOH, 1: 1 (B), FLOW: 15 ML/Min). The absolute stereochemistry of the two enantiomers corresponding to the two product peaks was not determined.

Peak 1: Chiral HPLC Rt=14.960 min (Column: REGIS (S,S) WHELK-01 (250×4.6mm×5 μ)); Mobile Phase: A: n-Hexane, B: 0.1% HCOOH IN ETHANOL: METHANOL (80:20); Flow: 1.0 ml/min). LCMS: Rt=1.253 min; MS m/z 332.80 [M+H]+; [Method 1]. $^1H$ NMR (300 MHZ, DMSO-$d_6$) δ 10.16 (brs, 1H), 8.33 (s, 1H), 8.28 (d, J=4.9 Hz, 1H), 7.20 (d, J=4.9 Hz, 1H), 5.75 (s, 1H), 5.60 (s, 1H), 5.02 (s, 1H), 4.90-4.79 (m, 2H), 3.44 (s, 3H), 2.96 (q, J=7.6 Hz, 2H), 1.26 (t, J=7.5 Hz, 3H).

Peak 2: Chiral HPLC Rt=18.565 min (Column: REGIS (S,S) WHELK-01 (250×4.6mm×5 μ)); Mobile Phase: A: n-Hexane, B: 0.1% HCOOH IN ETHANOL: METHANOL (80:20); Flow: 1.0 ml/min). LCMS: Rt=1.258 min; MS m/z 332.8 [M+H]+; [Method 1]. $^1H$ NMR (300 MHZ, DMSO-d6) δ 10.16 (brs, 1H), 8.35 (s, 1H), 8.30 (d, J=4.9 Hz, 1H), 7.23 (d, J=4.6 Hz, 1H), 5.76 (s, 1H), 5.60 (s, 1H), 5.03 (s, 1H), 4.93-4.75 (m, 2H), 3.44 (s, 3H), 2.97 (q, J=7.6 Hz, 2H), 1.26 (t, J=7.5 Hz, 3H).

Example 6: methyl (R)-4-(5-fluoro-4-((R)-1-fluoroethyl) pyridin-3-yl)-2-(fluoromethyl)-5-oxo-1,4,5,7-tetrahydrofuro [3,4-b]pyridine-3-carboxylate or methyl (R)-4-(5-fluoro-4-((S)-1-fluoroethyl) pyridin-3-yl)-2-(fluoromethyl)-5-oxo-1,4,5,7-tetrahydrofuro [3,4-b]pyridine-3-carboxylate

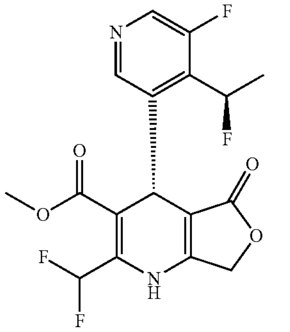

or

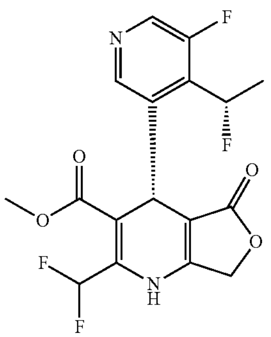

Step 1: ethyl (E)-4-acetoxy-2-((5-fluoro-4-(1-fluoroethyl) pyridin-3-yl)methylene)-3-oxobutanoate

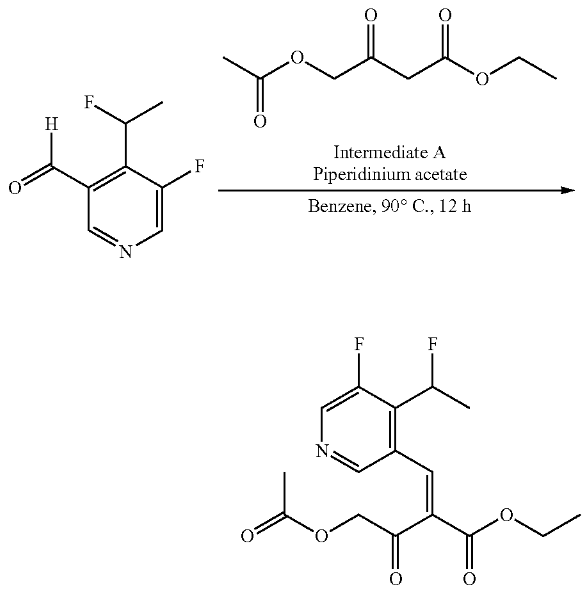

To a stirred solution of ethyl 4-acetoxy-3-oxobutanoate (1.49 g, 9.34 mmol) in benzene (50.00 mL) was added 5-fluoro-4-(1-fluoroethyl) nicotinaldehyde (from example 1 step 4, 1.60 g, 9.34 mmol), piperidinium acetate (0.135 g, 0.934 mmol) at RT and the reaction mixture was heated to 90° C. for 12 h. The solvent was removed under reduced pressure to afford crude compound. The crude product was purified by silica flash chromatography (25% ethyl acetate in hexane) to afford title compound as pale orange color syrup. ethyl (E)-4-acetoxy-2-((5-fluoro-4-(1-fluoroethyl) pyridin-3-yl)methylene)-3-oxobutanoate. LCMS: Rt=1.03 min & 1.35 min (Cis/Trans mixture); MS m/z 342.1 [M+H]+; [Method 2]. $^1$H NMR (300 MHZ, CDCl3) (Cis/Trans mixture, 1:1) δ 8.46 (s, 2H), 8.26 (s, 1H), 8.21 (s, 1H), 8.11-8.06 (m, 2H), 6.13-5.89 (m, 2H), 5.06 (s, 2H), 4.83 (s, 2H), 4.35 (d, J=7.0 Hz, 2H), 4.13 (d, J=6.9 Hz, 2H), 2.18 (s, 3H), 2.10 (s, 3H), 1.76-1.61 (m, 6H), 1.37 (d, J=7.2 Hz, 3H), 1.04 (d, J=7.2 Hz, 3H).

Steps 2 and 3:3'-ethyl 5'-methyl 2'-(acetoxymethyl)-6'-(dimethoxymethyl)-5-fluoro-4-(1-fluoroethyl)-1',4'-dihydro-[3,4'-bipyridine]-3',5'-dicarboxylate

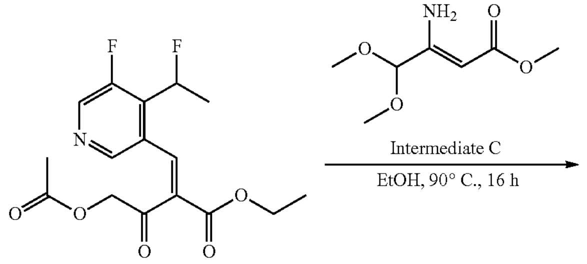

-continued

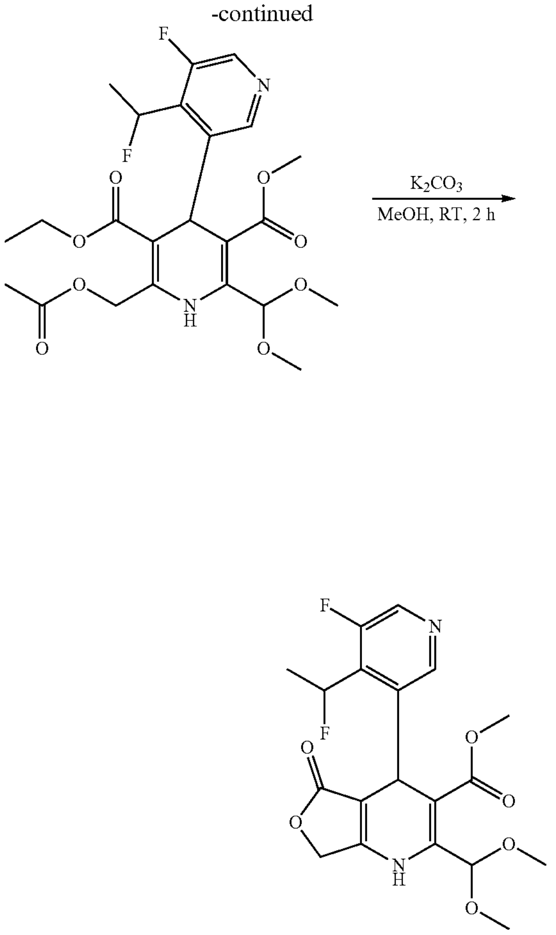

To a stirred solution of ethyl (E)-4-acetoxy-2-((5-fluoro-4-(1-fluoroethyl) pyridin-3-yl)methylene)-3-oxobutanoate (610.0 mg, 1.79 mmol) in EtOH (8.00 mL) was added methyl (Z)-3-amino-4,4-dimethoxybut-2-enoate (313.0 mg, 1.79 mmol) at RT and the reaction mixture was heated at 90° C. for 16 h. The solvent was removed under reduced pressure to afford crude compound as brown color syrup (0.96 g), which was used as such for next step.

To a solution of 3'-ethyl 5'-methyl 2'-(acetoxymethyl)-6'-(dimethoxymethyl)-5-fluoro-4-(1-fluoroethyl)-1',4'-dihydro-[3,4'-bipyridine]-3',5'-dicarboxylate (0.96 g, 1.92 mmol) in MeOH (10.00 mL), was added $K_2CO_3$ (0.53 g, 3.85 mmol) and the reaction mixture was stirred at RT for 2 h. The solvent was removed under reduced pressure, residue added to water and product extracted with EtOAc (3×50 mL). The combined organic layer was washed with brine, dried over anhydrous $Na_2SO_4$, and the solvent removed under reduced pressure. The crude product was purified by silica flash chromatography (40-80% ethyl acetate in hexane) to yield the desired product Methyl 2-(dimethoxymethyl)-4-(5-fluoro-4-(1-fluoroethyl) pyridin-3-yl)-5-oxo-1,4,5,7-tetrahydrofuro [3,4-b]pyridine-3-carboxylate as a brown solid. LCMS: Rt=1.105 min & 1.116 min (diastereomeric mixture); MS m/z 411.1 [M+H]+; [Method 1]. $^1$H NMR (300 MHZ, CDCl3) (diastereomeric mixture, 1:1) δ 8.39-8.22 (m, 4H), 7.44 (brs, 2H), 6.58-6.19 (m, 2H), 6.14 (s, 1H), 6.05 (s, 1H), 5.17 (s, 1H), 5.12 (s, 1H), 4.85-4.73 (m, 4H), 3.61 (s, 3H), 3.58 (s, 3H), 3.54 (s, 3H), 3.52 (s, 3H), 3.51 (s, 3H), 3.50 (s, 3H), 1.99-1.77 (m, 6H)

Step 4: methyl 4-(5-fluoro-4-(1-fluoroethyl) pyridin-3-yl)-2-formyl-5-oxo-1,4,5,7-tetrahydrofuro [3,4-b] pyridine-3-carboxylate

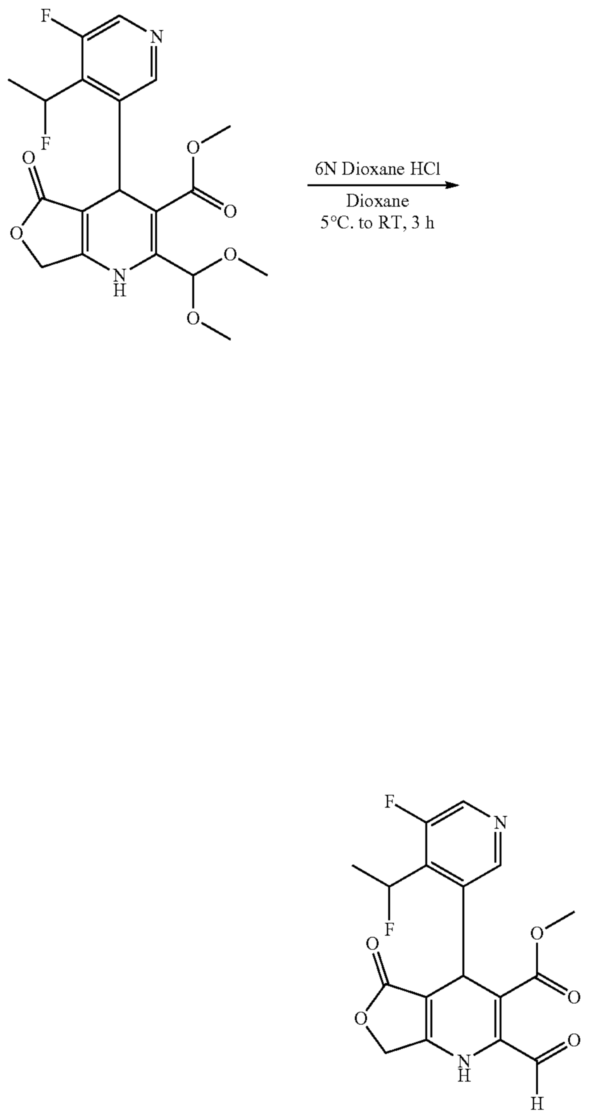

To a solution of methyl 2-(dimethoxymethyl)-4-(5-fluoro-4-(1-fluoroethyl) pyridin-3-yl)-5-oxo-1,4,5,7-tetrahydrofuro [3,4-b]pyridine-3-carboxylate (from step 6, 410.0 mg, 1.0 mmol) in dioxane (8.00 mL) was added 6N dioxane HCl (2.00 mL) at 5° C. and the reaction mixture was stirred at RT for 3 h. The solvent was removed under reduced pressure and diluted with EtOAc. EtOAc was washed with $NaHCO_3$ solution, brine, dried over anhydrous $Na_2SO_4$, and the solvent removed under reduced pressure to afford title compound methyl 4-(5-fluoro-4-(1-fluoroethyl) pyridin-3-yl)-2-formyl-5-oxo-1,4,5,7-tetrahydrofuro [3,4-b]pyridine-3-carboxylate. LCMS: Rt=1.089 min & 1.097 min (diastereomeric mixture); MS m/z 365.1 [M+H]+; [Method 1]. $^1$H NMR (300 MHZ, CDCl3) (diastereomeric mixture, ~1:1) δ 10.58 (s, 1H), 10.42 (s, 1H), 8.34-8.25 (m, 4H), 7.87 (s, 1H), 7.84 (s, 1H), 6.51-6.17 (m, 2H), 5.35 (s, 1H), 5.25 (s, 1H), 4.91-4.77 (m, 4H), 3.70 (s, 6H), 2.04-1.81 (m, 6H).

Step 5: methyl 2-(difluoromethyl)-4-(5-fluoro-4-(1-fluoroethyl) pyridin-3-yl)-5-oxo-1,4,5,7-tetrahydrofuro [3,4-b]pyridine-3-carboxylate

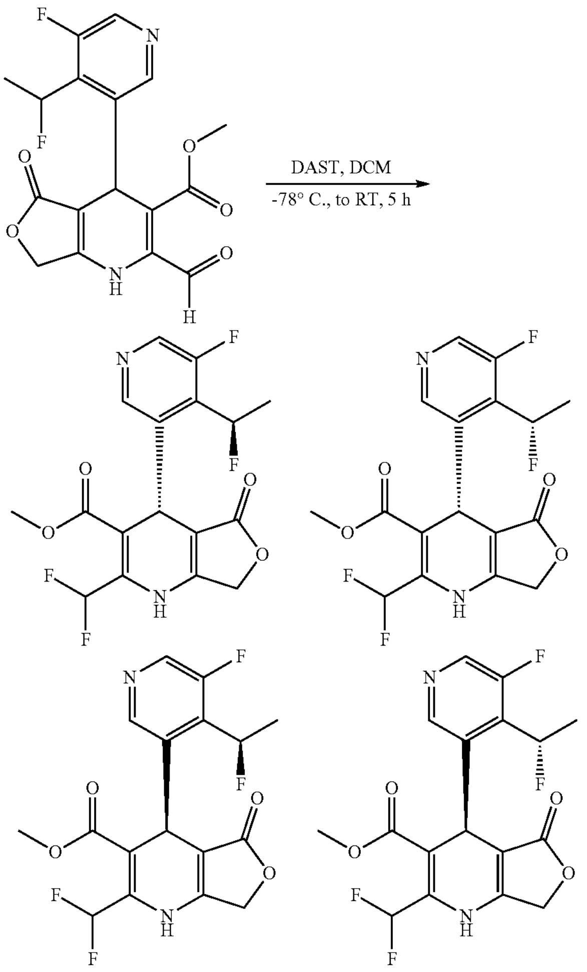

To a stirred solution of methyl 4-(5-fluoro-4-(1-fluoroethyl) pyridin-3-yl)-2-formyl-5-oxo-1,4,5,7-tetrahydrofuro [3,4-b]pyridine-3-carboxylate (from step 4, 90.0 mg, 0.247 mmol) in DCM (3.00 mL) was added DAST (0.065 mL, 0.49 mmol) at −78° C. and the reaction was stirred at RT for 5 h. Reaction was quenched with water at −30° C. and product extracted into DCM (3×10 mL). The combined organic layers were washed with $NaHCO_3$ solution, brine, dried over anhydrous $Na_2SO_4$, and the solvent removed under reduced pressure to afford crude compound.

rac-diastereomers were separated by Prep HPLC (Column: WATERSxBRIDGE (19×150 mm), 5.0 μ; Mobile Phase: A=WATER, B=ACN; Flow: 15 ml/min) to afford rac-diastereomer 1 and rac-diastereomer 2. The absolute stereochemistry of the four stereoisomers corresponding to the four product peaks was not determined.

rac-diastereomer 1 was separated into its enantiomers by chiral HPLC (Column: LUX CELLULOSE-4, 250 MM×21.2 MM×5 MICRON; Mobile Phase: A: Hexane: B: EtOH; Flow Isocratic: 15 mL/min).

rac-diastereomer 2 was separated into its enantiomers by chiral HPLC (Column: CHIRALPAK IJ, 250 MM×20

MM×5 MICRON; Mobile Phase: A: Hexane: B: EtOH: MeOH: 1:1; Flow Isocratic: 15 mL/min).

Example 6 is the first eluting peak from rac-diastereoisomer 2

Chiral HPLC Rt=4.486 min (Column: CHIRAL PAK-IJ (150×4.6 mm×5 μ)); Mobile Phase: A: n-Hexane, B: ETHANOL: METHANOL (50:50); Flow: 1.0 ml/min).

LCMS: Rt=0.4231 min; MS m/z 387.1 [M+H]+; [Method 2].

$^1$H NMR (400 MHZ, CD3OD) δ 8.31-8.30 (m, 2H), 7.50 (t, J=53.7 Hz, 1H), 6.43-6.26 (m, 1H), 5.26 (s, 1H), 4.89 (d, J=8.8 Hz, 2H), 3.59 (s, 3H), 1.87 (dd, J=23.0, 6.3 Hz, 3H) minus 1H Example 6a: Second eluting peak from rac-diastereoisomer 2

Chiral HPLC Rt=5.064 min (Column: CHIRAL PAK-IJ (150×4.6 mm×5p)); Mobile Phase: A: n-Hexane, B: ETHANOL: METHANOL (50:50); Flow: 1.0 ml/min).

LCMS: Rt=1.438 min; MS m/z 386.85 [M+H]+; [Method 1].

$^1$H NMR (400 MHZ, CD3OD) δ 8.31 (d, J=1.0 Hz, 1H), 8.25 (d, J=2.8 Hz, 1H), 7.46 (t, J=54.4 Hz, 1H), 6.42-6.26 (m, 1H), 5.23 (s, 1H), 4.79-4.73 (m, 2H), 3.55 (s, 3H), 1.85 (dd, J=23.3, 6.6 Hz, 3H) minus 1H.

Example 6b: First eluting peak from rac-diastereoisomer 1

Chiral HPLC Rt=5.830 min (Column: LUX CELLULOSE-4 (150×4.6mm×5 μ)); Mobile Phase: A: n-Hexane, B: ETHANOL: METHANOL (50:50); Flow: 1.0 ml/min).

LCMS: Rt=1.125 min; MS m/z 387.1 [M+H]+; [Method 1].

$^1$H NMR (400 MHZ, CD3OD) δ 8.31 (d, J=2.8 Hz, 1H), 8.24 (d, J=1.2 Hz, 1H), 7.46 (t, J=53.48 Hz, 1H), 6.56-6.40 (m, 1H), 5.24 (s, 1H), 4.87 (d, J=2.1 Hz, 2H), 3.59 (s, 3H), 1.79 (dd, J=23.2, 6.6 Hz, 3H) minus 1H Example 6c: Second eluting peak from rac-diastereoisomer 1

Chiral HPLC Rt=6.761 min (Column: LUX CELLULOSE-4 (150×4.6 mm×5 μ)); Mobile Phase: A: n-Hexane, B: ETHANOL: METHANOL (50:50); Flow: 1.0 ml/min).

LCMS: Rt=1.435 min; MS m/z 386.85 [M+H]+; [Method 1].

$^1$H NMR (400 MHZ, CD3OD) δ 8.31 (d, J=3.0 Hz, 1H), 8.24 (d, J=1.2 Hz, 1H), 7.46 (t, J=53.6 Hz, 1H), 6.56-6.40 (m, 1H), 5.24 (s, 1H), 4.87 (d, J=2.1 Hz, 2H), 3.59 (s, 3H), 1.79 (dd, J=23.0, 6.6 Hz, 3H) minus 1H.

Biological Data

Many known calcium channel activators have shown complex mechanisms of activating $Ca_v1.2$. These molecules not only increase peak currents, but also have additional mechanisms that increase intracellular calcium concentration, for example, by shifting the voltage sensitivity of the channel to more negative membrane potentials. FIG. 1 illustrates these additional mechanisms by depicting simulated cardiac action potentials from an epicardial environment and showing the impact of shifting the voltage of $Ca_v1.2$ activation to more negative membrane potentials at a Potential (mV) versus Time (ms). These additional mechanisms could drive or facilitate cardiovascular effects such as increase in blood pressure, change in heart rate or contractility, and/or arrhythmia due to QT prolongation. For example, the O'Hara-Rudy model was used to investigate the effect of $Ca_v1.2$ modulation on action potential duration and arrhythmic liability. It was identified that a >12 mV hyperpolarizing shift in the activation curve could potentially lead to >15% QT prolongation and an increased risk of arrhythmia. Therefore, minimizing any shifts in voltage sensitivity may lead to compounds with a reduced risk of QT prolongation and cardiac arrhythmia.

The compounds of formula (I) are highly potent $Ca_v1.2$ activators having a biophysical profile which minimizes the cardiovascular risks outlined above. First, the compounds of formula (I) limit their effects on the voltage sensitivity by minimizing hyperpolarizing shifts to <9 mV to mitigate for an arrhythmia potential. Second, the compounds of formula (I) increase $Ca_v1.2$ peak currents by no more than 2.5 fold, thereby limiting over-activation of the channel. Third, the compounds of formula (I) do not delay $Ca_v1.2$ channel inactivation, a pathophysiological mechanism underlying cardiac symptoms of Timothy Syndrome. Moreover, compounds of formula (I) are designed to maximize brain exposure by showing no significant efflux in the brain.

Generation and Maintenance of the $Ca_v1.2$-HEK293 (AUX) cell line

The monoclonal $Ca_v1.2$-HEK293 (AUX) cell line constitutively expresses human $Ca_v1.2$ alpha1 (α1) subunit (CACNA1C) and has doxycycline-inducible expression of the alpha2delta (α2Δ2) auxiliary subunit (CACNA2D2) and beta2 (β2) auxiliary subunit (CACNB2). To generate the cell line, expression vectors pcDNA5.0/FRT-TO-CACNA2D2-FCS-P2A-CACNB2 and pCMV6-entry-CACNA1C were established via gene synthesis and cloning. Here, pcDNA5.0/FRT-TO plasmid is from Invitrogen, pCMV6-entry is from Origene, FCS stands for Furin Cleavage Site, P2A is a peptide self-cleavage sequence derived from porcine teschovirus-1, and FRT is the Flippase recognition target site. Next, parental line Flp-In™ 293 T-Rex (Invitrogen) was transfected with pcDNA5.0/FRT-TO-CACNA2D2-FCS-P2A-CACNB2 and Flippase vector pOG44 (Invitrogen) to establish targeted integration of the CACNA2D2-FCS-P2A-CACNB2 expression cassette into the pre-engineered FRT site in Flp-In™ 293 T-Rex. This intermediate cell line was then transfected with pCMV6-entry-CACNA1C to establish stable CACNA1C expression. Clonal isolation was achieved under Neomycin selection. A cell clone (2-19B) with good voltage-dependent Barium current (see electrophysiology methods below) was selected for characterization of $Ca_v1.2$ activators.

To maintain the cell line, cells were passaged twice per week. At each passage, growth media (Table 1) were completely removed and cells were rinsed sequentially with 10 ml of D-PBS and 5 mL of warm TrypLE™ Express Enzyme (Gibco). Both D-PBS and TrypLE™ Express Enzyme were immediately removed afterrinsing. Plates were then placed at room temperature for 3-5 minutes. Next, 10 mL of warm 37° C. complete media was added to flush the cell-growing surface and collect dissociated cells. Cells were counted and seeded into new flasks, targeting a density of $2\text{-}3\times10^6$ cells per T175 $cm^2$ flask.

TABLE 1

| Growth medium for HEK293-$Ca_V$1.2(AUX) cells | |
|---|---|
| Reagent | Concentration |
| DMEM | |
| Heat inactivated fetal bovine serum | 10% |
| Hygromycin B | 100 ug/ml |
| Blasticidin | 10 ug/ml |
| Geneticin (G418) | 200 ug/mL |

Electrophysiological characterization of $Ca_v$1.2 activators using $Ca_v$1.2-HEK293 (AUX) cell line and QPatch 24 hours prior an electrophysiology experiment, doxycycline (1 μg/ml) was added to the growth medium (Table 1), and 25 UM of verapamil was co-applied to prevent calcium influx triggered cell death. Cell confluency should reach 70%-80% right before the experiment.

To harvest cells (from a T175 $cm^2$ flask as an example), growth media were removed completely, and the cells were rinsed with 10 ml of D-PBS. D-PBS was aspirated, and 10 ml of Detachin (Genlantis) was added and the plate was placed in a 37° C. incubator for 10 minutes. Detached cells were placed into a 15 ml conical tube and spun at 1000 rpm for 2 minutes. Supernatant was removed, and cells were re-suspended in QPatch complete media (Table 2) to desired cell density of 1.5-3 million cells per QPatch run. Each experimental run uses 1.5 mL of cells.

The cells suspension was taken to the Sophion QPatch platform that uses whole-cell voltage clamp to measure barium currents conducted through $Ca_v$1.2 on single-hole QPlates. Extracellular and intracellular patch clamp solutions are described in Tables 3 and 4, respectively. A dose-response assay protocol was used to determine the maximal fold change of peak inward current (Emax) and potency ($EC_{50}$) of each compound. The protocol had eight liquid periods. The first liquid period was to stabilize current amplitude, which was monitored using repetitive 200-ms voltage pulses stepping from −80 mV to 0 mV. The second liquid period was to determine baseline current amplitude in the presence of vehicle control, using a single 20-ms voltage pulse stepping from −80 mV to 0 mV. The third through eighth liquid periods were used to ascertain a 6-dose response to compound treatments, also using single 20-ms voltage pulses stepping from −80 mV to 0 mV. The $EC_{50}$ was generated using the following equation $I_{concentration}=I_{base}+(I_{full}-I_{base})*c^n/(XC_{50}{}^n+c^n)$, where c is the concentration and n is the Hill coefficient constant. $I_{full}$ is the maximal current achievable, and $I_{base}$ is 0. A channel biophysics assay protocol was used to determine channel gating properties including current-voltage relationship (IV curves), half-way channel activation voltage ($V_{1/2}$), rate of channel inactivation (tau), and amplitude of tail current. Among these, $V_{1/2}$ was derived from fitting equation $G(V)=G_{Vmin}+(G_{Vmax}-G_{Vmin})/(1+\exp(-(V-V_{1/2})/V_{slope}))$, where G stands for conductance, $G_{Vmin}$ equals 0, $G_{Vmax}$ is the maximal conductance, and $V_{slope}$ is a slope factor. G (V) was pre-calculated from equation $G(V)=I(V)/(V-0.06)$, for each experimentally applied depolarization potential (V) and the corresponding current amplitude (I(V)), and 0.06 in the equation was the experimentally determined reversal potential in volts. The protocol had four liquid periods. The first liquid period was to stabilize current amplitude, which was monitored using repetitive 200-ms voltage pulses stepping from −80 mV to 0 mV. Upon stabilization of current amplitude, a baseline value for the tau of inactivation was determined, via a single-exponential fit of the inactivation phase of the current trace. The second liquid period was to measure the baseline values constituting the current-voltage relationship in the presence of vehicle control, and the third liquid period was to measure the compound effect on the current-voltage relationship. During each of these two liquid periods, cells were given ten 20-ms voltage pulses, each stepping from −80 mV to an incremental value that ranges from −55 mV to +35 mV (increment size 10 mV). During the fourth liquid period a 200-ms voltage pulse from −80 mV to 0 mV was delivered again to measure the compound effect on tau of inactivation.

TABLE 2

| QPatch complete media: | |
|---|---|
| Reagent | Concentration |
| CHO-Serum free Media (SFM) | 25 mM |
| 1M HEPES | |

TABLE 3

| Extracellular solution for QPatch experiments | |
|---|---|
| Chemical | Concentration (mM) |
| Sodium Chloride | 145 |
| Barium Chloride | 10 |
| Potassium Chloride | 4 |
| HEPES (4-(2-hydroxyethyl)-1-piperazineethanesulfonic acid)) | 10 |
| HEPES | 10 |

pH to 7.4 with NaOH for a final osmolarity of ~315 mOSm, filter solution through 0.2 μM filter.

TABLE 4

| Intracellular solution for QPatch experiments. The solution is a mix of 80% part two (stored at −80° C.) and 20% part one: | |
|---|---|
| Chemical | Concentration (mM) |
| Part One: | |
| Cesium Fluoride | 135 |
| HEPES (4-(2-hydroxyethyl)-1-piperazineethanesulfonic acid)) | 10 |
| Sodium Chloride | 10 |
| EGTA (Ethylene glycol-bis(2-aminoethylether)-N,N,N',N'-tetraacetic acid) | 1 |
| pH to 7.2 with CsOH for a final osmolarity of ~295 mOSm, filter solution through 0.2 μM filter. | |
| Part Two: | |
| Cesium Chloride | 140 |
| EGTA (Ethylene glycol-bis(2-aminoethylether)-N,N,N',N'-tetraacetic acid) | 10 |
| HEPES (4-(2-hydroxyethyl)-1-piperazineethanesulfonic acid)) | 10 |
| Adenosine 5'-triphosphate magnesium salt | 5 |

pH to 7.2 with KOH for a final osmolarity of ~295 mOSm, filter solution through 0.2 μM filter.

Assessment of compound exposure-cFos induction (PK-PD) relationship in wild-type mice Animal maintenance and ethics. All animals were housed with regulated temperature and light cycle (22° C., 12-hour light/12-hour dark cycle) with unrestricted access to food and water. All animal experiments were performed in accordance with institutional guidelines for the care and use of laboratory animals as approved by the Institutional Animal Care and Use Committee (IACUC) of the Novartis Institutes for BioMedical Research, Inc. (Cambridge, MA, USA).

Compound administration and brain tissue collection. Wild-type $C_{57}$BL/6J male mice were obtained from Jackson laboratories (Bar Harbor, ME). The acute, single-dose effects of $Ca_v$1.2 activators of the present disclosure were evaluated in male eight-week old mice (n=6 mice per compound). Each compound was dissolved in 10% PEG300, 10% Solutol, 10% Cremophore EL, and 70% Phosphate Buffered Saline and administered intraperitoneal (i.p.) at a concentration of 1 mg/kg up to 30 mg/kg depending on the compound. Animals were euthanized one hour after compound administration via exsanguination under deep anesthesia. Blood was collected in EDTA tubes for downstream analysis of drug levels. Brains were rapidly removed from the skull, and the cerebral cortex and cerebellum were regionally dissected. Cerebellar samples were snap frozen in liquid nitrogen to assess compound exposure. Cortical samples for cFos assessment were placed in 500 L of RNAlater solution (ThermoFisher) to preserve the integrity of RNA in the sample. Samples remained in RNAlater for at least 24 hours at 4° C. before moving to −80° C. for storage before processing.

Quantification of cFos mRNA induction. Tissue homogenization was performed using TissueLyser system for 96 well plates (Qiagen). First, frozen cortical samples were thawed, removed from RNAlater, and placed into TissueLyser tubes along with Buffer RLT containing 0.5% Reagent DX and one 5 mm TissueLyser metal bead. The TissueLyser tubes were loaded into a TissueLyser II tissue homogenizer for 3 rounds of homogenization, with each round lasting 5 minutes at 30 Hz bead-beating frequency. Total RNA was purified from the homogenate using RNeasy 96 Plus kit (Qiagen), RNA concentration and A260/A280 ratio were quantified via the Nanodrop (ThermoFisher), and all samples were normalized to 100 ng/μl concentration. RNA was reverse transcribed into cDNA using the Superscript III First-strand synthesis SuperMix Kit (ThermoFisher). For each sample, 6 μl of RNA (600 ng total) was mixed with 1 μL of Oligo dT and 1 μL of annealing buffer and heated to 65° C. for 5 minutes. Next, 10 UL of 2× First-Strand Reaction Mix and 2 μL of the Enzyme mix were added to achieve a total reaction volume of 20 μL. The samples were heated to 50° C. for 50 minutes then 85° C. for 5 minutes to complete cDNA synthesis.

Quantitative PCR was performed on the cDNA samples using Quantitect Multiplex RT-PCR kit (Qiagen) in a 384-well assay format. Each PCR well contained 2 μL of cDNA (60 ng total), 10 μL of RT-PCR mastermix, 1 μL of cFos FAM Taqman probe (Mm00487425_m1 (FAM) #4351368), 1 UL of GAPDH VIC Taqman probe (Mm99999915-g1 (VIC) #4448486), 0.2 μL of Multiplex RT mix and 5.8 μl of RNase-free water. On the ViiA7 Real-Time PCR system (ThermoFisher), the samples were heated to 95° C. for 15 minutes then cycled between 94° C. for 45 seconds and 60° C. for 45 seconds for 45 cycles. cFos Ct values were exported, normalized to GAPDH Ct values, and converted to relative fold change in expression using the delta-delta Ct relative quantification method. cFos fold changes between compound treatments and vehicle were analyzed by one-way ANOVA, followed by Tukey's post-hoc comparisons.

Quantification of compound exposure. Cerebellar tissue samples were homogenized in 4 mL of 20% acetonitrile and 80% Phosphate buffered saline for every 1 g of tissue (5× dilution). Tissue was homogenized using either of the following three methods: hand held probe system, TissueLyser system with 5 mm steel bead at a frequency of 30 s-1 for 4 min, or OMNI Bead Ruptor Elite homogenizer for 30 seconds to 1 minute depending on tissue type. Tissue samples were added to a 96-well plate (12.5 μL sample) and processed for quantification by mass spectrometry.

Results

TABLE 5

Compound data

| Example | QPatch EC50 (uM) | QPatch Emax | Biophysics voltage shift (mV) | Brain: blood Ratio | %↑ cFOS mRNA cortex (3 mg/kg ip) |
|---|---|---|---|---|---|
| 1 | 0.22 | 3.3 | −6.6 | 0.2 | 174 |
| 2 | 0.061* | 2.2 | −5.9 | 1.5 | 384 |
| 3 peak 1 | 2.0 | 1.7 | nd | nd | nd |
| 4 peak 1 | 2.9 | 2.9 | nd | nd | nd |
| 5 peak 1 | >2.6 | 2.4 at 10 μM | nd | nd | nd |
| 6 | 0.25 | 2.5 | −5.6 | nd | nd |

QPatch was conducted as a 6-point dose response with 10 individual determinations at each concentration. Unless stated only one experimental replicate (n = 1)

*n = 2 nd = not determined

COMPARATIVE EXAMPLES

Other $Ca_v$1.2 activators are known, however these compounds are not as potent and/or do not have the desired biophysical properties needed to activate the channel and have sufficient brain exposure, while at the same time minimizing cardiovascular risks, such as increase in blood pressure, altered heart rate or contractility, and/or arrhythmia due to QT prolongation.

TABLE 6

| Comparative Example Number | Structure Name | QPatch EC50 (μM) | QPatch Emax | Biophysics voltage shift (mV) | Brain: blood ratio |
|---|---|---|---|---|---|
| Comparative examples to other known CaV1.2 activators | | | | | |
| Reported calcium channel activators (single enantiomers of reported racemates) showing various Qpatch profiles (Emax & V-shift) | | | | | |
| Comparative Example 1 | 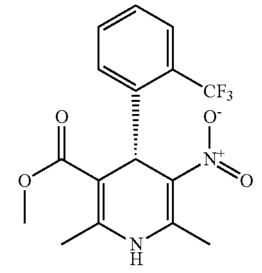 [SMILES: COC(=O)C1=C(C)NC(C)=C([N+](=O)[O-])[C@H]1c1ccccc1C(F)(F)F] (BayK8644) | 0.021 | 3.9 | −10.11 | Not determined |
| Comparative Example 2 | 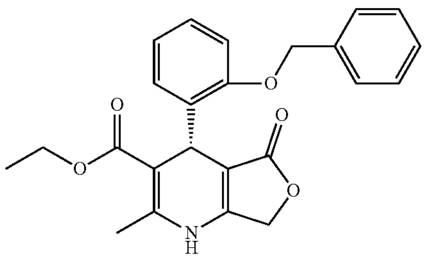 [SMILES: CCOC(=O)C1=C(C)NC2=C(C(=O)OC2)[C@H]1c1ccccc1OCc1ccccc1] (RS30124) | 0.45 | 4.3 | −15.4 | Not determined |
| Comparative Example 3 | 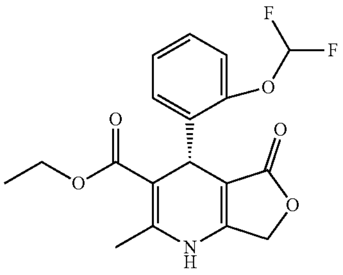 [SMILES: CCOC(=O)C1=C(C)NC2=C(C(=O)OC2)[C@H]1c1ccccc1OC(F)F] (CGP028392) | 0.28 | 2.2 | −6.7 | 0.23 |
| Comparative Example 4 | 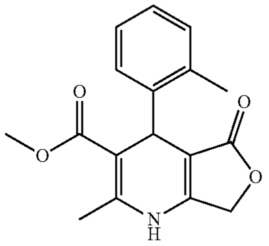 [SMILES: COC(=O)C1=C(C)NC2=C(C(=O)OC2)C1c1ccccc1C] CAS# 85825-32-7 | 2.24 | 1.4 | Not determined | Not determined |

TABLE 6-continued

| Comparative examples to other known CaV1.2 activators | | | | | |
|---|---|---|---|---|---|
| Comparative Example Number | Structure Name | QPatch EC50 (μM) | QPatch Emax | Biophysics voltage shift (mV) | Brain: blood ratio |
| Comparative Example 5 | 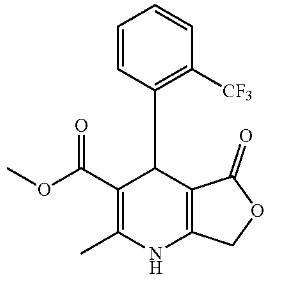 [SMILES: COC(=O)C1=C(C)NC2=C(C(=O)OC2)C1c1ccccc1C(F)(F)F] CAS# 85825-31-6 | 0.36 | 1.4 | −4.3 | Not determined |
| Comparative Example 6 | 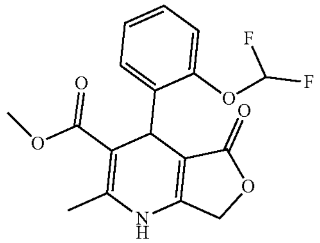 [SMILES: COC(=O)C1=C(C)NC2=C(C(=O)OC2)C1c1ccccc1OC(F)F] CAS# 92638-18-1 | 0.51 | 1.7 | −7.1 | Not determined |
| Comparative Example 7 | 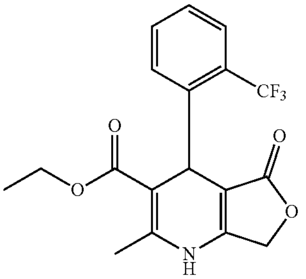 [SMILES: CCOC(=O)C1=C(C)NC2=C(C(=O)OC2)C1c1ccccc1C(F)(F)F] | 0.93 | 1.9 | Not determined | Not determined |

What is claimed is:

1. A compound according to formula (I) or a pharmaceutically acceptable salt thereof

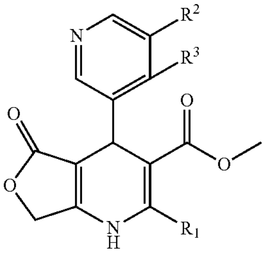

(I)

wherein:

$R^1$ is selected from $C_{1-6}$ alkyl and $C_{1-6}$ haloalkyl;

$R^2$ is selected from H and halo; and $R^3$ is selected from $C_{1-6}$ alkyl and $C_{3-8}$ cycloalkyl, each of which is optionally substituted with one to three halo.

2. A compound according to formula (I) or a pharmaceutically acceptable salt thereof

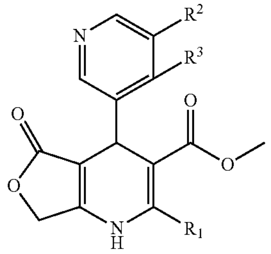

(I)

wherein:

$R^1$ is selected from $CH_3$, $CF_3$, $CHF_2$ and $CH_2F$;

$R^2$ is selected from H and F; and $R^3$ is selected from $C_{1-4}$ alkyl, cyclopropyl and cyclobutyl each of which is optionally substituted with one to three F.

3. The compound according to claim 1, wherein the compound is of formula (Ia), (Ia)

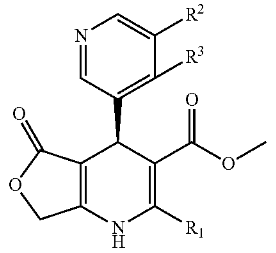

or a pharmaceutically acceptable salt thereof.

4. The compound according to claim 1, wherein the compound is of formula (Ib), (Ib)

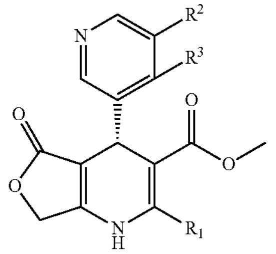

or a pharmaceutically acceptable salt thereof.

5. The compound or pharmaceutically acceptable salt thereof according to claim 1, wherein $R^1$ is $CH_3$.

6. The compound or pharmaceutically acceptable salt thereof according to claim 1, wherein $R^1$ is $CF_3$.

7. The compound or pharmaceutically acceptable salt thereof according to claim 1, wherein $R^1$ is $CHF_2$.

8. The compound or pharmaceutically acceptable salt thereof according to claim 1, wherein $R^1$ is $CH_2F$.

9. The compound or pharmaceutically acceptable salt thereof according to claim 1, wherein $R^2$ is H.

10. The compound or pharmaceutically acceptable salt thereof according to claim 1, wherein $R^2$ is F.

11. The compound or pharmaceutically acceptable salt thereof according to claims 1, wherein $R^3$ is $C_1$-4 alkyl which is optionally substituted with one to three F.

12. The compound or pharmaceutically acceptable salt thereof according to claim 1, wherein $R^3$ is cyclopropyl which is optionally substituted with one to three F.

13. The compound or pharmaceutically acceptable salt thereof according to claim 1, wherein $R^3$ is cyclobutyl which is optionally substituted with one to three F.

14. The compound according to claim 1, wherein the compound is selected from the group consisting of:

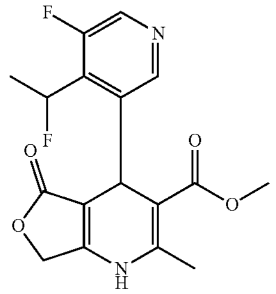

methyl 4-(5-fluoro-4-(1-fluoroethyl)pyridin-3-yl)-2-methyl-5-oxo-1,4,5,7-tetrahydrofuro[3,4-b]pyridine-3-carboxylate

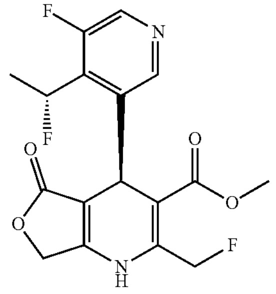

methyl (S)-4-(5-fluoro-4-((R)-1-fluoroethyl)pyridin-3-yl)-2-(fluoromethyl)-5-oxo-1,4,5,7-tetrahydrofuro[3,4-b]pyridine-3-carboxylate

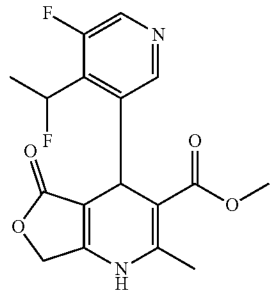

methyl (S)-4-(5-fluoro-4-((R)-1-fluoroethyl)pyridin-3-yl)-2-methyl-5-oxo-1,4,5,7-tetrahydrofuro[3,4-b]pyridine-3-carboxylate

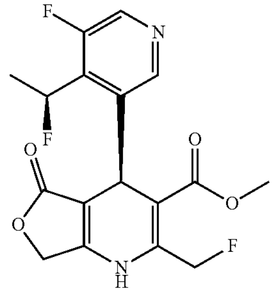

methyl (S)-4-(5-fluoro-4-((S)-1-fluoroethyl)pyridin-3-yl)-2-(fluoromethyl)-5-oxo-1,4,5,7-tetrahydrofuro[3,4-b]pyridine-3-carboxylate -continued

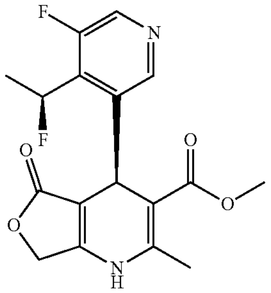

methyl (S)-4-(5-fluoro-4-((S)-1-fluoroethyl)pyridin-3-yl)-2-methyl-5-oxo 1,4,5,7-tetrahydrofuro[3,4-b]pyridine-3-carboxylate

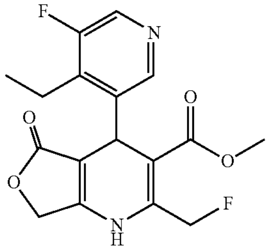

methyl 4-(4-ethyl-5-fluoropyridin-3-yl)-2-(fluoromethyl)-5-oxo-1,4,5,7-tetrahydrofuro[3,4-b]pyridine-3-carboxylate

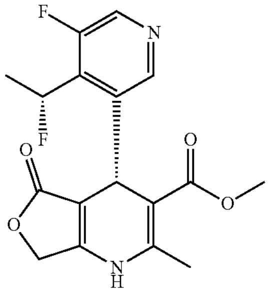

methyl (R)-4-(5-fluoro-4-((R)-1-fluoroethyl)pyridin-3-yl)-2-methyl-5-oxo-1,4,5,7-tetrahydrofuro[3,4-b]pyridine-3-carboxylate

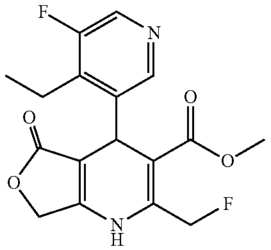

methyl (R)-4-(4-ethyl-5-fluoropyridin-3-yl)-2-(fluoromethyl)-5-oxo-1,4,5,7-tetrahydrofuro[3,4-b]pyridine-3-carboxylate -continued

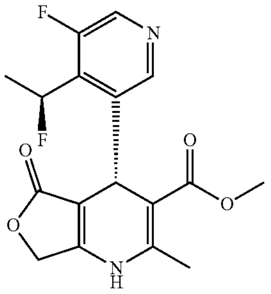

methyl (S)-4-(5-fluoro-4-((S)-1-fluoroethyl)pyridin-3-yl)-2-methyl-5-oxo-1,4,5,7-tetrahydrofuro[3,4-b]pyridine-3-carboxylate

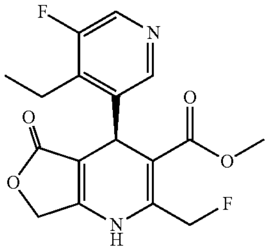

methyl (S)-4-(4-ethyl-5-fluoropyridin-3-yl)-2-(fluoromethyl)-5-oxo-1,4,5,7-tetrahydrofuro[3,4-b]pyridine-3-carboxylate

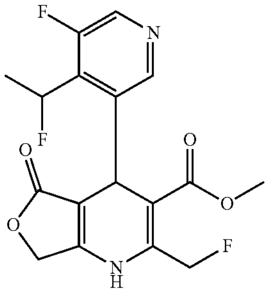

methyl 4-(5-fluoro-4-(1-fluoroethyl)pyridin-3-yl)-2-(fluoromethyl)-5-oxo-1,4,5,7-tetrahydrofuro[3,4-b]pyridine-3-carboxylate

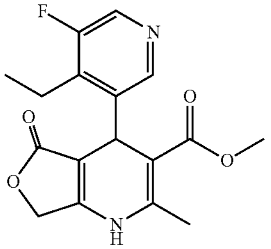

methyl 4-(4-ethyl-5-fluoropyridin-3-yl)-2-methyl-5-oxo-1,4,5,7-tetrahydrofuro[3,4-b]pyridine-3-carboxylate -continued

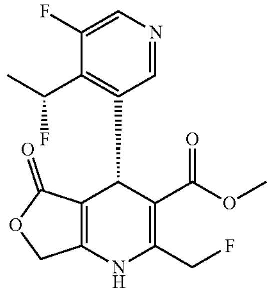

methyl (R)-4-(5-fluoro-4-((R)-1-fluoroethyl)pyridin-3-yl)-2-(fluoromethyl)-5-oxo-1,4,5,7-tetrahydrofuro[3,4-b]pyridine-3-carboxylate

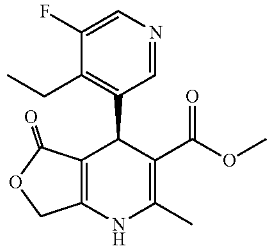

methyl (S)-4-(4-ethyl-5-fluoropyridin-3-yl)-2-methyl-5-oxo-1,4,5,7-tetrahydrofuro[3,4-b]pyridine-3-carboxylate

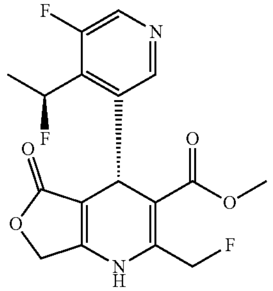

methyl (R)-4-(5-fluoro-4-((S)-1-fluoroethyl)pyridin-3-yl)-2-(fluoromethyl)-5-oxo-1,4,5,7-tetrahydrofuro[3,4-b]pyridine-3-carboxylate

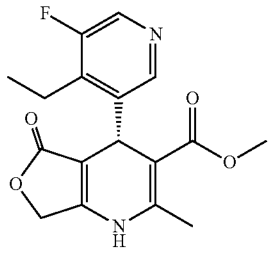

methyl (R)-4-(4-ethyl-5-fluoropyridin-3-yl)-2-methyl-5-oxo-1,4,5,7-tetrahydrofuro[3,4-b]pyridine-3-carboxylate -continued

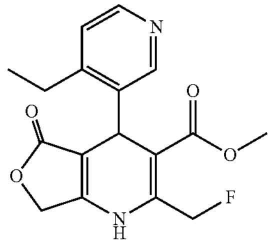

methyl 4-(4-ethylpyridin-3-yl)-2-(fluoromethyl)-5-oxo-1,4,5,7-tetrahydrofuro[3,4-b]pyridine-3-carboxylate

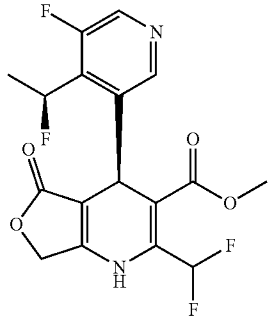

methyl (S)-2-(difluoromethyl)-4-(5-fluoro-4-((S)-1-fluoroethyl)pyridin-3-yl)-5-oxo-1,4,5,7-tetrahydrofuro[3,4-b]pyridine-3-carboxylate

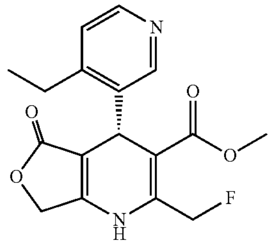

methyl (R)-4-(4-ethylpyridin-3-yl)-2-(fluoromethyl)-5-oxo-1,4,5,7-tetrahydrofuro[3,4-b]pyridine-3-carboxylate

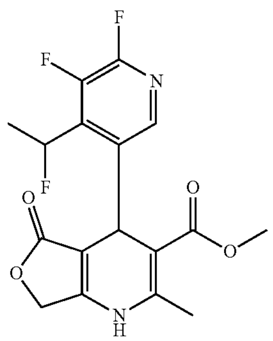

methyl 4-(5,6-difluoro-4-(1-fluoroethyl)pyridin-3-yl)-2-methyl-5-oxo-1,4,5,7-tetrahydrofuro[3,4-b]pyridine-3-carboxylate -continued

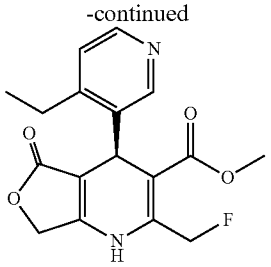

methyl (S)-4-(4-ethylpyridin-3-yl)-2-(fluoromethyl)-5-oxo-1,4,5,7-tetrahydrofuro[3,4-b]pyridine-3-carboxylate

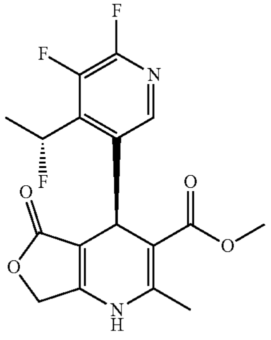

methyl (S)-4-(5,6-difluoro-4-((R)-1-fluoroethyl)pyridin-3-yl)-2-methyl-5-oxo-1,4,5,7-tetrahydrofuro[3,4-b]pyridine-3-carboxylate

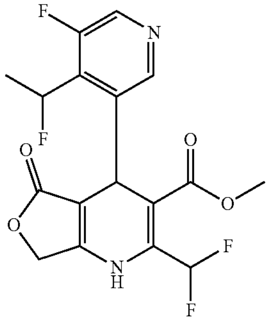

methyl 2-(difluoromethyl)-4-(5-fluoro-4-(1-fluoroethyl)pyridin-3-yl)-5-oxo-1,4,5,7-tetrahydrofuro[3,4-b]pyridine-3-carboxylate

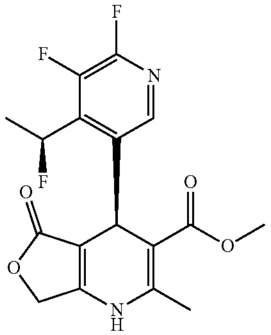

methyl (S)-4-(5,6-difluoro-4-((S)-1-fluoroethyl)pyridin-3-yl)-2-methyl-5-oxo-1,4,5,7-tetrahydrofuro[3,4-b]pyridine-3-carboxylate -continued

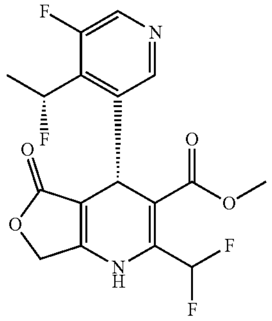

methyl (R)-2-(difluoromethyl)-4-(5-fluoro-4-((R)-1-fluoroethyl)pyridin-3-yl)-5-oxo-1,4,5,7-tetrahydrofuro[3,4-b]pyridine-3-carboxylate

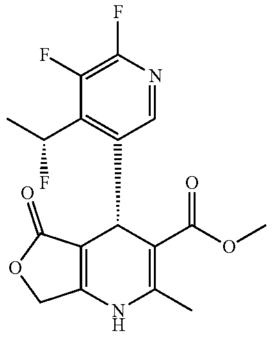

methyl (R)-4-(5,6-difluoro-4-((R)-1-fluoroethyl)pyridin-3-yl)-2-methyl-5-oxo-1,4,5,7-tetrahydrofuro[3,4-b]pyridine-3-carboxylate

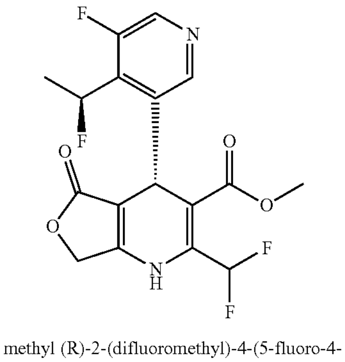

methyl (R)-2-(difluoromethyl)-4-(5-fluoro-4-((S)-1-fluoroethyl)pyridin-3-yl)-5-oxo-1,4,5,7-tetrahydrofuro[3,4-b]pyridine-3-carboxylate -continued

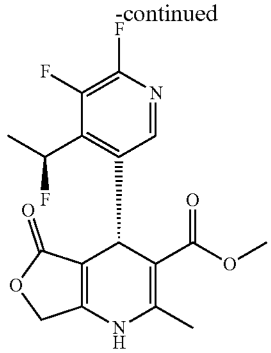

and methyl (R)-4-(5,6-difluoro-4-((S)-1-fluoroethyl)pyridin-3-yl)-2-methyl-5-oxo-1,4,5,7-tetrahydrofuro[3,4-b]pyridine-3-carboxylate

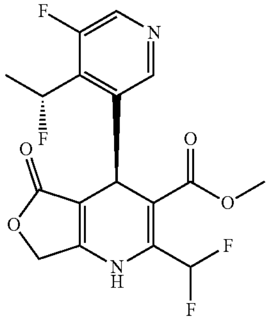

methyl (S)-2-(difluoromethyl)-4-(5-fluoro-4-((R)-1-fluoroethyl)pyridin-3-yl)-5-oxo-1,4,5,7-tetrahydrofuro[3,4-b]pyridine-3-carboxylate, or a pharmaceutically acceptable salt thereof.

15. A pharmaceutical composition comprising a compound according to claim 1, or a pharmaceutically acceptable salt thereof, and a pharmaceutically acceptable excipient.

16. A method of treating psychiatric disorders, neurodevelopmental disorders, neurodegenerative disorders or cardiac conditions in a subject in need thereof, the method comprising administering to the subject a therapeutically effective amount of a compound according to claim 1, or a pharmaceutically acceptable salt thereof.

17. The method according to claim 16, wherein the psychiatric disorders are selected from schizophrenia, bipolar disorder, major depressive disorder, and substance use disorder;

the neurodevelopmental disorders are selected from ADHD, Phelan McDermid Syndrome, and autism spectrum disorder;

the neurodegenerative disorders are selected from multiple sclerosis, frontotemporal dementia, and Alzheimer's disease; and the cardiac conditions are selected from Brugada Syndrome, Short QT syndrome, and early repolarization syndrome.

* * * * *